(12) United States Patent
Brahme et al.

(10) Patent No.: US 9,259,595 B2
(45) Date of Patent: Feb. 16, 2016

(54) POSITRON EMITTER IRRADIATION SYSTEM

(75) Inventors: Anders Brahme, Danderyd (SE); Marta Lazzeroni, Sundbyberg (SE)

(73) Assignee: RADINOVA AB, Danderyd (SE)

( * ) Notice: Subject to any disclaimer, the term of this patent is extended or adjusted under 35 U.S.C. 154(b) by 408 days.

(21) Appl. No.: 13/821,328

(22) PCT Filed: Sep. 6, 2011

(86) PCT No.: PCT/SE2011/051077
§ 371 (c)(1),
(2), (4) Date: Mar. 7, 2013

(87) PCT Pub. No.: WO2012/033453
PCT Pub. Date: Mar. 15, 2012

(65) Prior Publication Data
US 2013/0172658 A1 Jul. 4, 2013

Related U.S. Application Data

(60) Provisional application No. 61/380,963, filed on Sep. 8, 2010.

(51) Int. Cl.
*A61N 5/10* (2006.01)
*G21G 1/10* (2006.01)
*G21G 4/08* (2006.01)

(52) U.S. Cl.
CPC ............... *A61N 5/10* (2013.01); *A61N 5/1048* (2013.01); *G21G 1/10* (2013.01); *G21G 4/08* (2013.01); *A61N 5/1071* (2013.01); *A61N 2005/1052* (2013.01); *A61N 2005/1087* (2013.01); *A61N 2005/1095* (2013.01)

(58) Field of Classification Search
CPC ............... A61N 5/10; A61N 5/1077; A61N 2005/1085; A61N 2005/1087
See application file for complete search history.

(56) References Cited

U.S. PATENT DOCUMENTS

2007/0225603 A1 9/2007 Jackson
2009/0134345 A1* 5/2009 Gentry et al. ............. 250/503.1
2010/0301228 A1* 12/2010 Pu .............................. 250/396 R

FOREIGN PATENT DOCUMENTS

WO WO 2005/053794 A1 6/2005

OTHER PUBLICATIONS

Korejwo et al., "The measurement of isotropic cross sections of 12C beam fragmentation on liquid hydrogen at 3.66 GeV/nucleon," J. Phys. G: Nucl. Part. Phys. 26, 2000, p. 1171-1186.*

(Continued)

*Primary Examiner* — Charles A Marmor, II
*Assistant Examiner* — Thaddeus Cox
(74) *Attorney, Agent, or Firm* — Birch, Stewart, Kolasch & Birch, LLP

(57) ABSTRACT

Analysis of the production of $^{11}C$ fragments mainly by projectile fragmentation of a stable monodirectional and monoenergetic primary $^{12}C$ beam in different decelerating materials are presented and the optimal target choice have been identified to obtain the highest possible beam quality of decelerated $^{11}C$ beam at arbitrary energies and therapeutic ranges. The optimal $^{11}C$-generating target is made of hydrogen preferably followed by a digitally variable decelerator of a hydrogen rich compound, such as polyethylene, to maximize the quality of the $^{11}C$ beam.

23 Claims, 25 Drawing Sheets

(56) References Cited

OTHER PUBLICATIONS

Inaniwa et al., "Quantitative Comparison of Suitability of Various Beams for Range Monitoring with Induced [beta]+ Activity in Hadron Therapy", Institute of Physics Publishing, Physics in Medicine and Biology 50 (2005), No. 6, pp. 1131-1145.

Lazzeroni et al., "Production of Clinically Useful Positron Emitter Beams During Carbon Ion Deceleration", Physics in Medicine and Biology 56 (2011) pp. 1585-1600.

Schardt et al., "Heavy-ion Tumor Therapy: Physical and Radiobiological Benefits", Reviews of Modern Physics, vol. 82, Jan.-Mar. 2010, pp. 383-425.

Schwender, "Design of a Monochromatizing Wedge Decelerator for Therapeutic Positron Emitting Light Ion Beams", Bachelor of Science Thesis, Medical Radiation Physics at Karolinska Institutet, School of Engineering Sciences, Department of Physics Royal Institute of Technology, pp. 1-33, Jun. 2011.

J.R. Alonso, et al., "High Purity Radioactive Beams at the BEVALAC", IEEE Transactions on Nuclear Science, vol. NS-26, No. 3, Jun. 1979, 3 pages.

L. Sihver, et al., "Present Status and Validation of HIBRAC", Radiation Measurements 44 (2009), pp. 38-46.

\* cited by examiner

Design of a Flexible Wedge System for Variable $^{11}$C Energies

1. Perpendicular Rotating Wedge

2. Variable Liquid Wedge

3. Two Axially Rotating Wedges

4. Digital Multi Layer Wedges

POSITRON EMITTER IRRADIATION SYSTEM

This application is the National Phase of PCT/SE2011/051077 filed on Sep. 6, 2011, which claims priority under 35 U.S.C. 119(e) to the U.S. Provisional Application No. 61/380,963 filed on Sep. 8, 2010, all which are hereby expressly incorporated by reference into the present application.

TECHNICAL FIELD

The embodiments generally relate to ion beam radiation, and in particular to the production of positron emitting ion radiation beams useful in ion radiation therapy to increase their visibility during PET or PET-CT imaging.

BACKGROUND

Accurate monitoring of the delivered dose and response of the tumor and surrounding normal tissue is a key issue in external beam radiation therapy. For light ion therapy, this is particularly important since their sharp depth dose distributions and steep lateral beam profile should be accurately located to allow optimal use of their high physical and biological selectivity and minimize normal tissue morbidity. The high energy density released at the end of the particle range generates a sharp dose maximum at the Bragg peak which is important to locate in the target volume of the patient. In light ion therapy, particularly with ions heavier than hydrogen and helium, this knowledge becomes most critical due to the fact that the mentioned physical selectivity is accompanied also by an increased biological efficiency and selectivity caused by the high local ionization density and cell inactivation around the Bragg peak. At present on-line PET-CT or off-line PET imaging are the only diagnostic technique that allow non-invasive three-dimensional (3D) in vivo monitoring of the dose delivered to the patient. The possibility of having information on the energy absorbed by the tissues with high energy Bremsstrahlung photon therapy has been investigated extensively by measuring the activity produced trough photonuclear reactions with the target nuclei. Due to the uncertainty of stopping powers in light ion therapy, range control and dose verification with ion beams are being studied in some centers. For light ions with atomic numbers below 4, range determination is not possible by positron emitting beams. However, nuclear reactions between the incoming particles and the nuclei of the tissue may cause positron activation along the beam path similar to photon beams. Unfortunately, this activity is much lower and less specific for characterizing the strong therapeutic dose delivery in the tumor. The lightest positron emitting projectiles are $_8$B, $^{9\text{-}10\text{-}11}$C, $^{13\text{-}12}$N and $^{15\text{-}14\text{-}13}$O and are therefore of particular increased interest for radiation therapy. Ions from oxygen and heavier ions are generally of too high ionization density in the normal tissues to be really suited for complication free curative radiation therapy. Generally with cyclotrons and sometimes with synchrotrons the generated ions with a maximum extracted energy in the 400 MeV/u energy range are combined with material decelerators to reduce the energy to clinically useful values.

In case of irradiation with stable carbon ion beams, the PET signal is mainly produced by nuclear fragmentation where several of the products are positron emitters: $^{11}$C, $^{15}$O, $^{10}$C, $^{13}$N nuclei, with half life respectively equal to 20 min, 2 min, 19 s and 10 min. The rather sharp maximum in the activity distribution due to $^{11}$C ions produced by projectile fragmentation can be used for gathering information about the penetration depth of the incoming particles due to their close energy-range relation in the medium. However, the background level is high and the Bragg peak in a heterogeneous patient is often difficult to accurately localize with most PET cameras. Furthermore, since the momentum transferred from incoming particles to the nuclei in the tissue is small and spread out, the activity due to target fragmentation reactions can only be used to estimate the localization of the plateau region of the beam. This approach therefore presents difficulties in establishing the precise correspondence between the dose delivered and the activity produced, since the signal is low and the origin of the activity is physically different and more disperse. Moreover, the PET signal produced is quite low for imaging purposes (200 Bq Gy$^{-1}$ cm$^{-3}$ for $^{12}$C).

An alternative approach was developed in the secondary beam line of the Heavy Ion Medical Accelerator (HIMAC) at the National Institute of Radiological Sciences (NIRS) in Chiba based on the experience from the early 70s at Lawrence Berkley Laboratory, where the possibility of using radioactive beams of $^{19}$Ne and $^{11}$C for treatment planning verification and therapy was proposed. At the Japanese ion facility the use of radioactive beams for range verification preceding the treatment with $^{12}$C stable or radioactive beams is still under study. This approach is mainly limited by the fact that the production rate of the secondary beam is quite low (between 0.1 and 1% of the primary $^{12}$C beam intensity depending on the angular acceptance achieved).

Therefore, by using radioactive beams the difficulty of linking the positron activation registered with the PET camera and dose delivered is largely overcome and the geometrical uncertainty due to the difference between the annihilation point recorded by the positron camera and the stopping point of the generated $^{11}$C particles in the tissue is gone. Most importantly, the use of a positron emitting therapeutic beam of $^{11}$C increases the specificity of imaging the Bragg peak about 50-fold.

Moreover, radioactive beams of $^8$B, $^9$C, $^{10}$C and $^{11}$C have been shown to have interesting proprieties as compared to the corresponding heavier stable beams due to their improved radiation quality, reduced fragmentation tail, low plateau LET and potentially increased biological efficiency through apoptosis (programmed cell death) induction in the Bragg peak region. Furthermore, from a clinical and radiation quality point of view, ion beams like $^9$C or $^8$B are characterized by emitting delayed low energy particles like protons and/or alpha particles at the end of the particle range that will further increase the local effectiveness of the treatment.

SUMMARY

In external beam radiation therapy, radioactive beams offer the best clinical solution to simultaneously treat and in vivo monitor the dose delivery using the most accurate diagnostic tools, such as PET or PET-CT imaging. However, difficulties mainly linked to the low production efficiency have so far limited their use. The present document is devoted to the optimization of the production of $^{11}$C fragments mainly by projectile fragmentation of a stable monodirectional and monoenergetic primary $^{12}$C beam in different decelerating materials to identify the optimal target choice and collection method to obtain high quality therapeutic $^{11}$C beams.

According to the embodiments a device for producing a $^{11}$C beam from a primary $^{12}$C beam is disclosed herein. The device comprises a decelerator comprising hydrogen (H$_2$) and is configured to produce and output a $^{11}$C beam that is suitable for external radiation therapy from the primary $^{12}$C beam that is incident on the decelerator.

Embodiments also define a radiation system comprising such a device and a method of producing a therapeutic quality $^{11}C$ beam from a primary $^{12}C$ beam by directing the primary $^{12}C$ beam through a decelerator comprising hydrogen to thereby obtain the desired $^{11}C$ beam and preferably separate it from contaminating fragments.

BRIEF DESCRIPTION OF THE DRAWINGS

The invention, together with further objects and advantages thereof, may best be understood by making reference to the following description taken together with the accompanying drawings, in which:

FIG. 3A illustrates the results for an incoming primary $^{12}C$ ion beam of 400 MeV/u for several target materials, both elements and compounds. For a few materials (liquid hydrogen, water and beryllium) a comparison between Monte Carlo results (symbols) and the least-squares fit based on the analytical model (equation (7)) is also shown (solid lines). FIG. 3B illustrates the case of a decelerator composed of a combination of two materials: 70 cm of liquid hydrogen (about 4.97 g/cm$^2$) and the remaining length made in polyethylene ($C_2H_4$). Results are shown in correspondence with two energy values of the incoming primary $^{12}C$ ion beam: 400 and 430 MeV/u. Dotted straight lines are drawn between data points.

DETAILED DESCRIPTION

Figure 1:
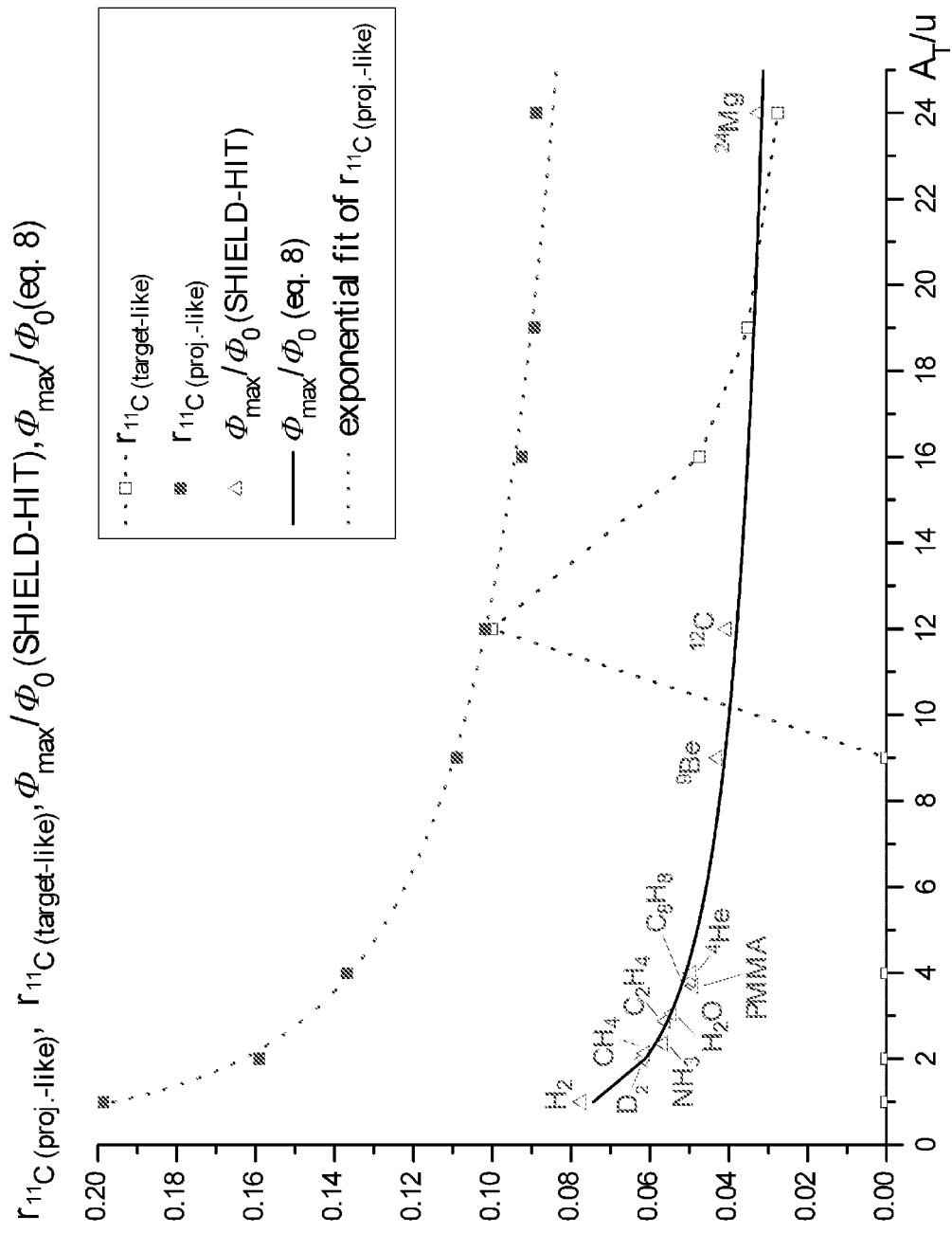
FIG. 1 is an illustration of the variation of the branching ratio between the reaction cross section $\sigma_{r,0}$ and the cross-section of production of projectile-like and target-like $^{11}C$ fragments ($\sigma_{11_C}$) as a function of the mass number of the medium ($A_T$): $r_{11_{C(proj.-like)}}$ (solid squares) and $r_{11_{C(target-like)}}$ (open squares) respectively. Values have been calculated using the MSDM (Many Stage Dynamic Model) generator of inelastic nuclear reactions. An exponential fit of the branching ratio data relative to the production of projectile-like $^{11}C$ fragments is also showed (dotted line) ($y=ax^b$ with $a=0.196$, $b=-0.264$). The solid curve on the bottom part of the figure shows instead the variation of the fluence build-up maximum as a function of the mass number of the target material. Empty triangles represent values of the fluence build-up maxima calculated by SHIELD-HIT and extracted from curves shown in FIGS. 3A and 3B.

The present embodiment generally relates to methods and devices of producing $^{11}$C positron emitting ions and in particular to the production of $^{11}$C positron emitting ions from a beam of $^{12}$C.

Herein, an investigation of the optimal choice of decelerating material for maximizing the production of high energy $^{11}$C positron emitting ions by the interaction of the incoming low emittance beam of $^{12}$C is presented. The quantity and quality of the $^{11}$C radioactive beam is studied here in terms of the relative fluence and mean energy as a function of the decelerating material and its thickness and energy remaining when exiting the decelerator.

Fragment Production

When a light ion beam penetrates a thick target, it undergoes nuclear reactions with the target atoms and its slowing-down process is affected by nuclear fragmentation reactions that lead to the attenuation of the incoming beam and the build-up of various primary beam and target like fragments. In the energy range of interest in radiation therapy, fragmentation reactions are mostly due to peripheral collisions between the incoming projectile and the target nucleus. The incident particle interacts primarily with the surface of the target nucleus and, consequently, a few nucleons may be stripped from the nuclei of the interacting atoms, resulting either in fragments with lower charge (charge-changing reactions), or in neutron deficient, not seldom positron emitting isotopes (non charge-changing reactions).

Fragments generated from the target nuclei are emitted almost isotropically, whereas projectile-like fragments are characterized by a narrow Gaussian-shaped momentum distribution centered on the incoming ion velocity and an angular distribution described by a narrow forward-directed Gaussian spread.

Assuming the same velocity of projectile-like fragments and primary ions, the range of such fragments in the material of interest could be estimated by the following relation:

$$R_s \approx \frac{A_s / Z_f^2}{A_p / Z_p^2} \times R_p \qquad (1)$$

where $A_s$, $A_p$ and $Z_f$, $Z_p$ are respectively the molar mass and charge of secondary fragments and primary ions and $R_p$ is the range of incoming primary ions.

This indicates that fragments of lower charge Z have longer range in the material, while neutron deficient fragments such as $^{11}$C initially have slightly shorter range than the primary beam. The mentioned advantageous proprieties of secondary positron emitting projectile fragments make them ideally suited for therapeutic purposes.

The Fluence Build-Up of Projectile Fragments

The secondary fragments created at different depths and transported through the phantom are attenuated and eventually stopped similar to the primary ions. Many different procedures have been developed during the years in order to derive analytical formulas describing the reaction cross-sections. One of the possible approaches is to consider the reaction cross-section $\sigma_r(E)$ as the product of an energy dependent factor $f(E)$ and a constant term $\sigma_{r,0}$ according to:

$$\sigma_r(E) = \sigma_{r,0} \times f(E) \quad (2)$$

The energy independent part $\sigma_{r,0}$ has different values at least for proton-nucleus and other nucleus-nucleus cross-sections. Reversely, the energy dependent factor, in the high energy region above about 110 MeV/u, could be assumed to have the same value independent of the charge of the target or projectile.

However, since our purpose is to focus on the dependency of cross-sections on the characteristics of the target material, in the first approximation the total energy independent reaction cross-section may be approximated by:

$$\sigma_{r,0} = \pi(R_T + R_p - b)^2 = \pi R_0^2 \left(A_T^{\frac{1}{3}} + A_p^{\frac{1}{3}} - b\right)^2 \quad (3)$$

where $R_T$, $A_T$, $R_p$, $A_p$ are respectively the nuclear radius and atomic mass number of the target and projectile ion and $R_0$ is the nuclear radius proportionality constant. b is the mean overlap parameter required for the interaction to take place and it takes into account the probability that, given a certain impact parameter, the projectile passes the target without resulting in any interaction. In the original derivation of this formula, the parameter b was considered as independent both of target and projectile molar masses. However, in a more accurate formulation, the $b(A_T, A_p)$ parameter could be assumed to be a second-order polynomial expression in $$A_p^{-\frac{1}{3}} \text{ and } A_T^{-\frac{1}{3}}$$

that reduces the cross-section value as the target and projectile mass number increases (cf. equation (4) and (5)).

Two different semi-empirical formulas for the reaction cross-sections can thus be used in order to describe the interaction of a fixed beam of $^{12}C$ ions in all the considered target media. The former formula was originally derived to describe proton-nucleus reaction cross-sections and, according to the invariance of the cross-sections for inverse kinematics, it could be used in the hydrogen target case.

$$\sigma_{r,0}(p, A_T) = \pi R_0^2 \left(1 + A_T^{\frac{1}{3}} - \left(2.247 - 0.915\left(1 + A_T^{-\frac{1}{3}}\right)\right)\left(1 + A_T^{-\frac{1}{3}}\right)\right)^2 \quad (4)$$

In the present case, with $^{12}C$ as a projectile incident in a liquid hydrogen target $A_T = 12$ and the reaction cross section assumes the value of about 221 mb. For all the other materials a nucleus-nucleus semi-empirical reaction cross section formula was instead proposed:

$$\sigma_{r,0}(A_T, A_P) = \quad (5)$$
$$\pi R_0^2 \left(A_T^{\frac{1}{3}} + A_P^{\frac{1}{3}} - \left(1.581 - 0.876\left(A_P^{-\frac{1}{3}} + A_T^{-\frac{1}{3}}\right)\right)\left(A_P^{-\frac{1}{3}} + A_T^{-\frac{1}{3}}\right)\right)^2$$

By defining the branching ratio between the partial cross-section or the specific reaction channel of interest $\sigma_i$ and the reaction cross-section $\sigma_{r,0}$ as $r_{i,T}$, the partial cross-section $\sigma_i$ relative to the production of secondary fragments can then be expressed as:

$$\sigma_i = \sigma_{r,0} \times r_{i,T} \quad (6)$$

with $\sigma_{r,0}$ given either by equation (4) or (5) depending to the considered material. The branching ratio describes the probability of obtaining a certain fragment (i) in a given collisional event.

The fluence build-up of secondary fragments can be described analytically by:

$$\frac{\Phi_i(z)}{\Phi_0^p} = \int_0^z \sigma_i \times n \times e^{-\mu_p s} e^{-\mu_f (z-s)} ds \quad (7)$$
$$\approx r_{i,T} N_A \rho_T \sigma_{r,0} \left(\frac{e^{-\mu_f z} - e^{-\mu_p z}}{\mu_p - \mu_f}\right) \text{ for } z \leq R_p$$

where $\mu_p$ and $\mu_f$ are respectively the mass attenuation coefficients of primaries and fragments. The first exponential factor in the integral above describes the attenuation of the primaries and thus the yield of fragments at a certain depth s in the target, while the second one takes into account the loss of produced fragments in the remaining target length and $R_p$ is the practical or continuous slowing down range of primary ions. This equation therefore describes the build-up of fragments from all upstream layers of the decelerator. Moreover, in order to include the effect of the finite range of the primaries, equation (7) should be multiplied by a range straggling cut-off factor that is close to unity for $z \leq R_p$ and rapidly goes to zero beyond $R_p$, such as a high-power Gaussian like function $$e^{-\left(\frac{z^2}{\sigma_z^2}\right)^N}$$

with $N \approx 10\text{-}15$ depending on the amount of range straggling.

Furthermore, by integrating the simple analytical expression in equation (7) and setting the derivative equal to zero, we obtain:

$$\frac{\Phi_{f,max}(z)/\Phi_{p,0} = r_{i,T}(\mu_p/\mu_f)^{1/(1-\mu_p/\mu_f)} = r_{i,T}(\sigma_p/\sigma_f)}{\sigma_f^{1/(1-\sigma_p/\sigma_f)} \approx 0.375 r_{i,T}} \quad (8)$$

since the mass attenuation coefficient is linked to the total reaction cross-section by the relation: $\mu = \sigma_{r,0} \times n$ and the factor $(\sigma_p/\sigma_f)^{1/(1-\sigma_p/\sigma_f)}$ has almost a constant value of 0.375 for the relevant materials.

Furthermore, the effective molar mass for compounds may be estimated from:

$$A_{eff} = \frac{\sum_i A_i N_i (\Phi_{f,max}/\Phi_{p,0})(A_i)/(\Phi_{f,max}/\Phi_{p,0})(H)}{\sum_i N_i} \quad (9)$$

where $N_i$ is the number of atoms of a certain element in the compounds, $A_i$ is the molar mass of the single element, $(\Phi_{f,max}/\Phi_{p,0})(A_i)$ is the normalized value of the fluence build-up maximum evaluated for a target corresponding to the element i and $(\Phi_{f,max}/\Phi_{p,0})(H)$ is the value of the normalized fluence build-up maximum evaluated for a hydrogen target.

Mean Energy of Primaries And Fragments

The mean energy $\overline{E}(z)$ at the depth z of the primary ions is analytically linked to the mean energy at the surface of the phantom $\overline{E_0}$ by the relation:

$$\overline{E_p}(z) = \overline{E_0}\left(1 - \frac{z}{R_0}\right)^{S_0 R_0/\overline{E_0}} \quad (10)$$

where $S_0$ is the initial total stopping power and $R_0$ is the range in the continuous slowing down approximation.

In case of secondary fragments generated by projectile fragmentation of the incoming primary beam, the mean energy at the depth z in the target material can also be analytically described by a somewhat more complex equation based on the depth dependence of the mean energy of the primary particles:

$$\overline{E_f}(z) = \frac{\int_0^z \overline{E_0^f}(s)\left(1 - \frac{z-s}{R_0^f(s)}\right)^{S_0^f(s) R_0^f(s)/\overline{E_0^f}(s)} \sigma_i n e^{-\mu_p s} e^{-\mu_f (z-s)} ds}{\int_0^z \sigma_i n e^{-\mu_p s} e^{-\mu_f (z-s)} ds} \quad (11)$$

where the mean energy of fragments at the surface $\overline{E_0^f}(z)$ is calculated by scaling the correspondent initial mean energy of the primaries taking into account the mass ratio of primary and secondary ions due based on the basic assumption that projectile fragments and primary ions have almost the same velocity. The formula showed in equation (10) is valid both at a depth lower than the practical range $R_p$ and in the region beyond, provided that, in the latter case, the upper limit of the integral is set to $R_p$.

SHIELD-HIT Code

The Monte Carlo code SHIELD-HIT07 has been used for the evaluation of the production of $^{11}C$ in $^{12}C$ ion beams in order to investigate the optimal choice of target material for maximizing the production of fast positron emitting isotopes that could be used for treatment and monitoring of the absorbed dose distribution. The SHIELD-HIT code is a transport code able to simulate the interaction of hadrons and nuclei in complex macroscopic targets. The inelastic nuclear reactions in the code are based on the Many Stage Dynamical Model (MSDN). In particular, to calculate total cross-section and nuclear reaction cross-sections SHIELD-HIT uses fits of a representative set of experimental data based on Optical model of nuclear reactions (above 200 MeV) and simple empirical formulas at lower energies. The code can handle a wide energy range from 2 GeV/Li to 25 KeV/u and, in case of neutrons, down to thermal energies. The MSDM generator of nuclear inelastic interaction cross sections has been used in order to evaluate the branching ratio of partial and reaction cross-sections $r_{i,T}$. Among other features, it also allows to separate low energy recoils and fast projectile like nuclear products.

The spatial distribution of the energy deposited by primary particles, nuclear fragments, recoil nuclei and charged secondary particles from neutron interaction as well as the fluence differential in energy of primary ions, fragments and higher order generations can be generated by the code. Both multiple Coulomb scattering and energy loss straggling are taken into account.

Irradiation Conditions

A monoenergetic and monodirectional beam of primary $^{12}C$ ions impinges on the axis of a cylindrical decelerator. The target is composed of slices with 10 cm of radius and 1 cm in thickness, for a total length of 300 cm. The composition of the medium has been varied over a wide range of materials: water ($H_2O$), PMMA ($C_5O_2H_8$), beryllium ($^9Be$), graphite ($^{12}C$), liquid hydrogen ($^1H$), liquid methane ($CH_4$), liquid deuterium, aluminum ($^{13}Al$), magnesium ($^{12}Mg$), liquid heavy water ($D_2O$), liquid ammonia ($NH_3$), helium ($^4He$), polystyrene ($C_8H_8$) and polyethylene ($C_2H_4$). Since the geometry of the target is fixed, a long phantom was chosen in order to allow the complete visualization of the build-up of the $^{11}C$ fragments in all the different materials considered in this study.

The energy of the primary $^{12}C$ beam was 400 MeV/u. However, in order to study the characteristics of the beam for energy regions corresponding to more deeply seated tumors, a further study at 430 MeV/u was also conducted. The mentioned analysis was performed for a decelerator composed by a combination of two media: a first section of 70 cm in length made of liquid hydrogen and the remaining length of polyethylene.

Results

FIG. 1 shows values of $r_{i,T}$ in correspondence of the production of projectile-like and target-like $^{11}C$ fragments for some selected target materials ($H_2$, $D_2$, $^4He$, $^9Be$, $^{12}C$, $^{16}O$, $^{19}F$ and $^{24}Mg$).

As expected, the target-like contribution to the $^{11}C$ fragment production is zero in case of light materials such as $Hz$, $^4He$ or $^9Be$, where the only available channel of production comes from projectile nucleus fragmentation. In the particular case of $^{12}C$ target instead the contribution to the $^{11}C$ production is almost equally distributed between target and projectile nuclei. Furthermore, the factor $r_{11C(proj.-like)}$ corresponding to the projectile-like $^{11}C$ production shows a higher value in case of lighter target materials, being the highest in case of hydrogen. Since projectile-like $^{11}C$ are mainly produced in peripheral interactions between $^{12}C$ primaries and the target nuclei, it is natural that neutron depleting reaction probability is higher in case of smaller and lighter targets. This can also be understood from probabilistic and geometric considerations since the hydrogen nuclei have very similar mass as the neutrons and are thus very efficient for neutron ejection. A function of the form $ax^b$ was fitted to the data shown as the dotted line in FIG. 1.

The fitting function of $r_{11C(proj.-like)}$ and the quasi-constant value of the factor $(v_p/\sigma_f)^{1/(1+\delta_p'\delta_f)}$ were used in order to evaluate values of the fluence build-up maximum for different target materials. Results of these calculations are showed in the solid curve in the figure below and compared with Monte Carlo calculations indicated as open triangles. Monte Carlo data of the fluence build-up maxima of compounds are showed in correspondence of $A_{\it eff}$ values calculated by SHIELD-HIT and the corresponding value on the solid curve previously evaluated by using equation (9) in case of pure element targets, confirming the applicability of the $A_{\it eff}$ formula.

Furthermore, it is interesting to compare nuclear reaction cross-section values calculated by the MSDM generator used by SHIELD-HIT with experimental results, other codes (FLUKA, GEANT4) and the cross-section value presented in equation (4) and (5).

Figure 2:
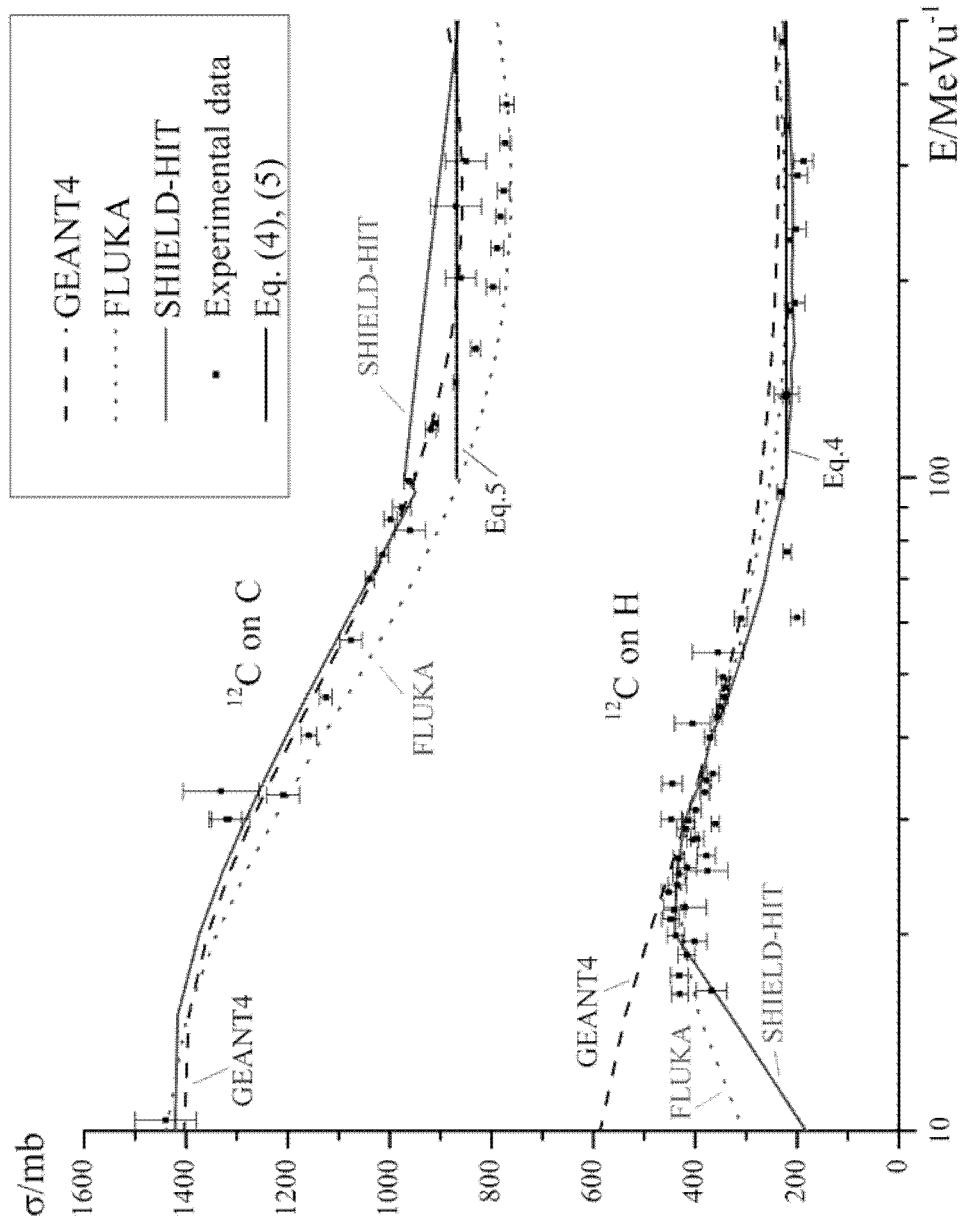
FIG. 2 illustrates a comparison of the energy dependence of the nuclear reaction cross-section used for a primary $^{12}C$ beam with $^{12}C$ (upper curves) and hydrogen (lower curves) used by different codes (FLUKA (dotted line), GEANT4 (dashed line), SHIELD-HIT (full line)) with experimental results and cross-section formulas described in equation (4) and (5).

In FIG. 2 nuclear reaction cross-sections of the interaction of $^{12}$C primary ion beam with $^{12}$C (upper curves) or H (lower curves) targets are presented with the corresponding semi-empirical cross-section values. In the high energy region (>100 MeV/u) for $^{12}$C on $^{12}$C-target values resulting from calculations made with the three codes are notably different, whereas, at lower energies, a better agreement between the codes is instead shown.

For the hydrogen case, differences between codes and experimental data as well are less evident and mostly notable in the region below 20 MeV/u. Moreover, for energies higher than 100 MeV/u the experimental data trend seems to be rather accurately reproduced by SHIELD-HIT.

The parameterization of nucleus-nucleus reaction cross sections is calculated by the SHIELD-HIT code from piece-wise smooth expressions which may not accurately join at the boundary points of the energy intervals. Thus, discontinuities such as the one seen in FIG. 2 at about 100 MeV/u in the reaction cross section for $^{12}$C on $^{12}$C-target are obtained.

With respect to the semi-empirical cross-sections values, the assumption of the independence of the cross-sections from the energy is further justified by the fact that the ratio of the integral of different cross-sections in the low energy region (<110 MeV/u) is approximately equal to the ratio of the high energy cross-section values. In fact, since our approach is mostly focused on comparisons between different target materials, this information has been considered as satisfactory.

Figure 3A:
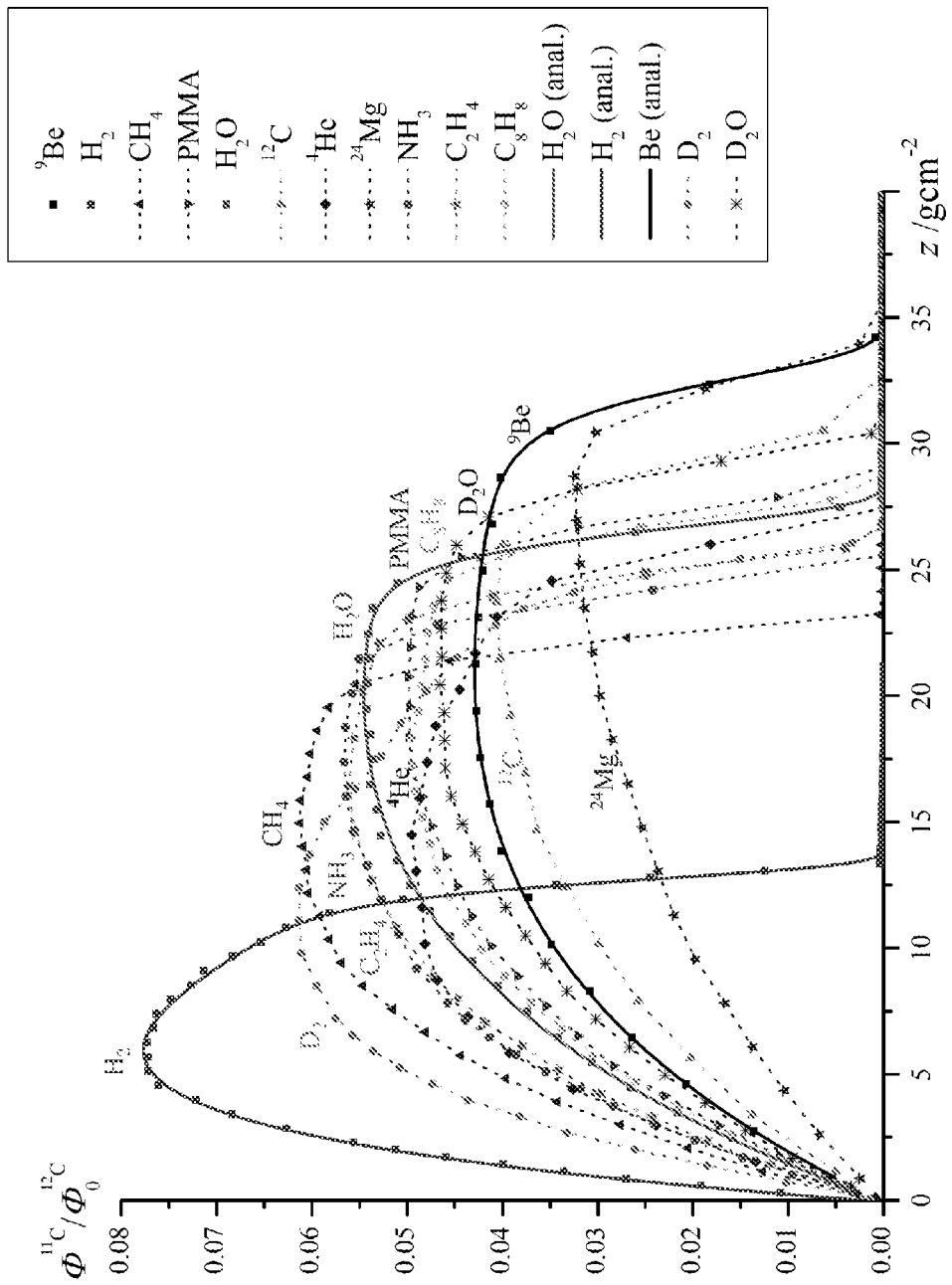
FIGS. 3A and 3B illustrate the fluence of positron emitting $^{11}C$ fragments produced by the fragmentation of a primary $^{12}C$ beam in different decelerating materials as a function of depth in the target (g/cm$^2$).

The fluence of both primary particles and fragments is calculated by the Monte Carlo code by scoring track lengths within each slice of the target. Therefore by plotting the fluence of generated fragments as a function of the depth in the phantom (FIGS. 3A and 3B), the contribution of target-like fragments is negligible as compared to projectile-like fragments. In fact, the fluence and length covered by those target-like fragments in each slice is very small and the energy low so the useful part of the build-up of the secondary $^{11}$C beam can be considered as mostly composed by fast projectile fragments.

The fluence of secondaries has been normalized to the primary fluence recorded in the first slice of the phantom (1 cm of length) and the depth in the material is here expressed in g/cm$^2$.

In case that a decelerator is composed of a single element, the results show that a higher fluence level is reached for lighter materials. In case of compound materials, the $^{11}$C production is affected by the number of hydrogen atoms composing the medium. The results show an enhancement in the generation of fast $^{11}$C secondary fragments for materials where the fraction by weight of hydrogen is higher such as liquid methane (CH$_4$), liquid ammonia (NH$_3$) and polyethylene (C$_2$H$_4$).

Figure 3B:
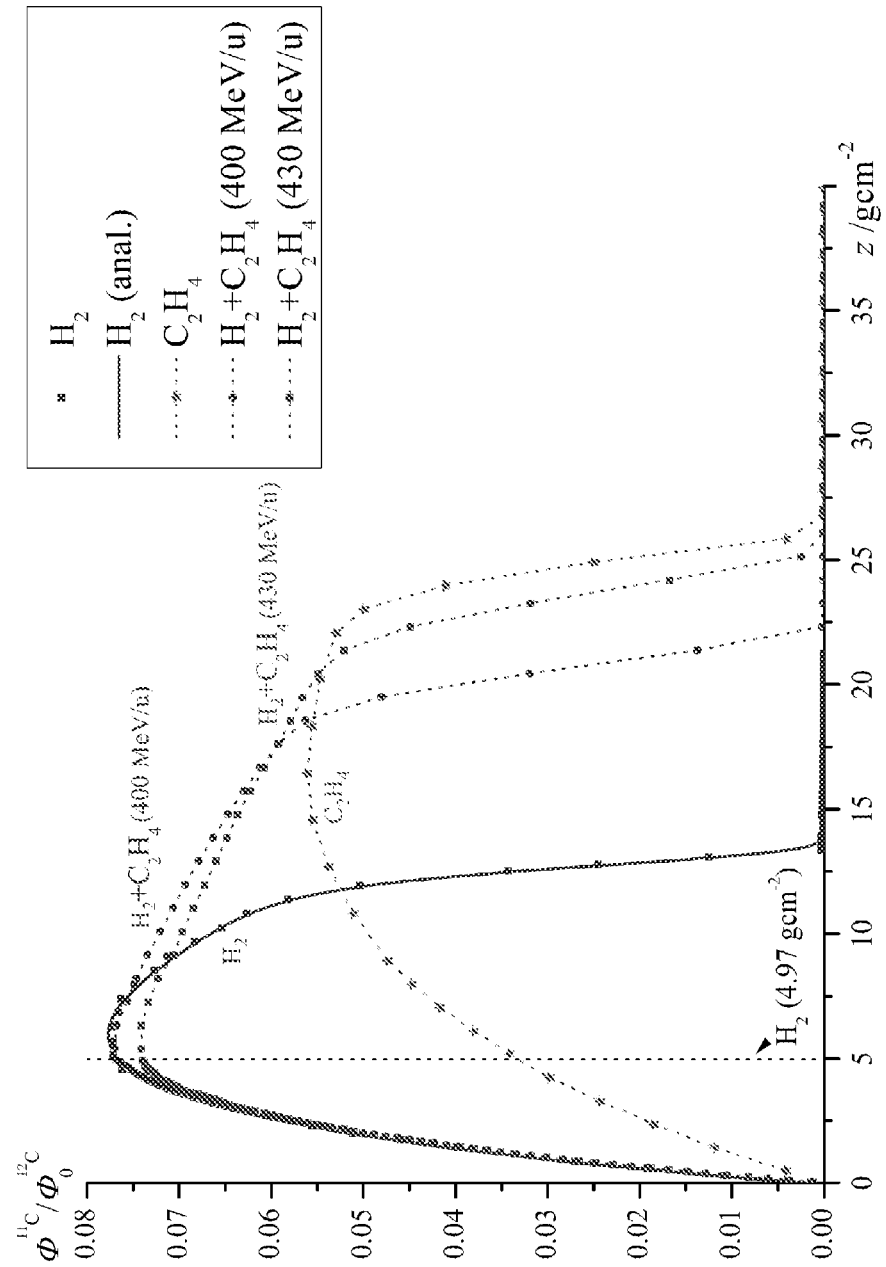

In FIG. 3B, the build-up of the fluence in a decelerator composed by two media is also shown: 70 cm of liquid hydrogen and the remaining 230 cm of polyethylene (C$_2$H$_4$). For the same combination of materials, the $^{11}$C fragments production has been further analyzed for a higher energy value 430 MeV/u.

In the particular case of liquid hydrogen, the level of maximum fluence is almost twice of that produced in beryllium, which is a common material used for radioactive beam production.

Moreover, for a few selected materials (liquid hydrogen, beryllium and water), a comparison between the analytical model described by equation (7) is also shown using the Gaussian-like factor mentioned above. The shape of the curves is very well reproduced by the analytical model.

Figure 4:
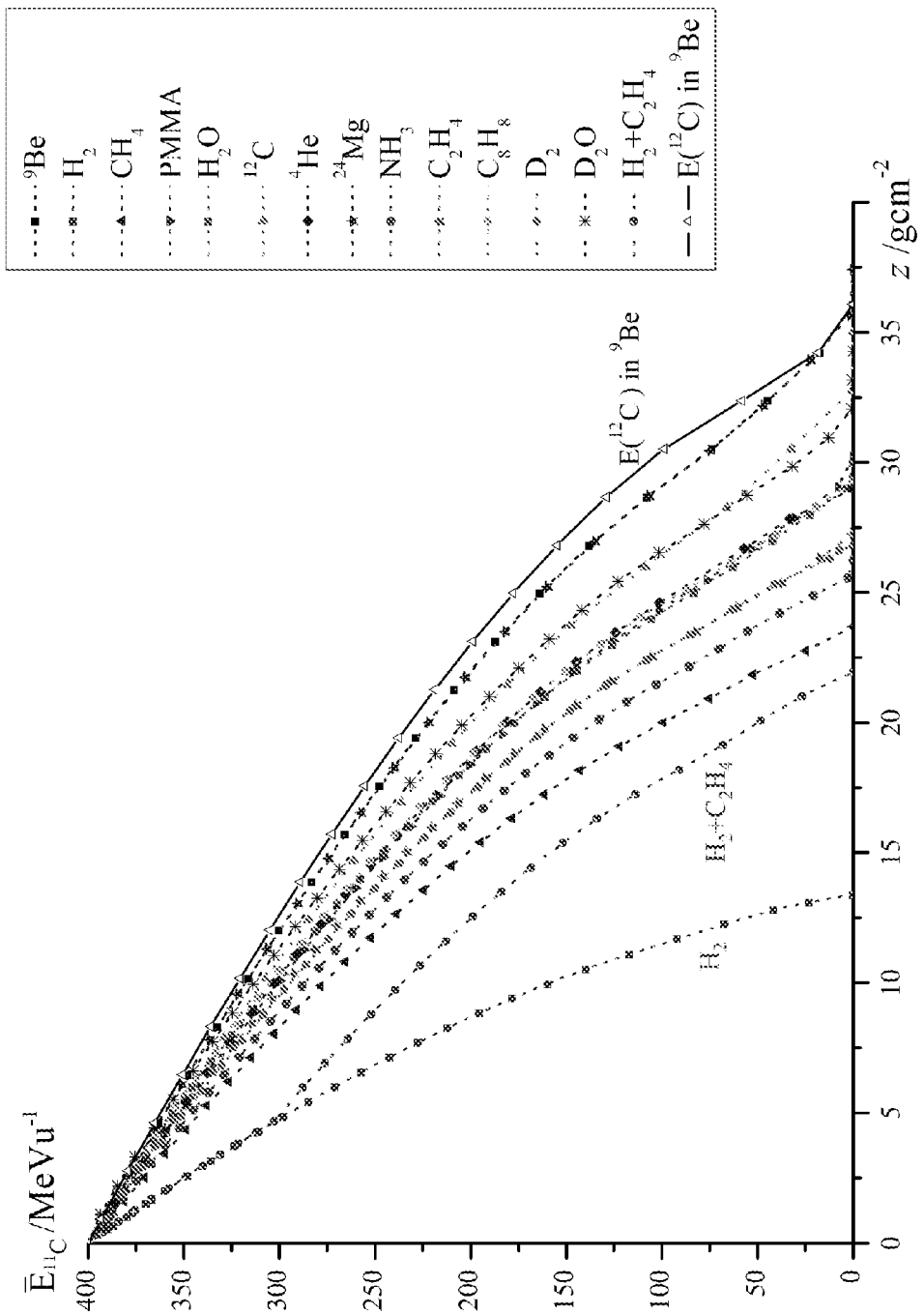
FIG. 4 illustrates the mean energy variation of the secondary beam of $^{11}C$ fragments as a function of the depth in different target materials (g/cm$^2$). The energy of the $^{12}C$ incoming beam has a fixed value of 400 MeV/u. In case of $^9Be$ the mean energy variation of a primary $^{12}C$ beam is also shown (solid line). Due to the close energy-range relations of primary $^{12}C$ and $^{11}C$ secondary ions, the shapes of the curves are very similar. Dotted straight lines are drawn between data points.

The variation of the mean energy of the beam (MeV/u) has been studied as a function of the depth in the target (g/cm$^2$) and results are presented in FIG. 4.

In the same figure, for the $^9$Be case, the mean energy variation with the depth of primary $^{12}$C ions is also showed. Due to the close energy and range relation in the medium, a similar shape of the mean energy variation as a function of the depth is observed both in case of the primary $^{12}$C beam and in case of $^{11}$C secondary beam. The observed bending of the $^{11}$C fragment mean energy curve is probably due to the presence of low energy $^{11}$C fragments generated in proximity of the end of the $^{12}$C ion range.

Figure 5A:
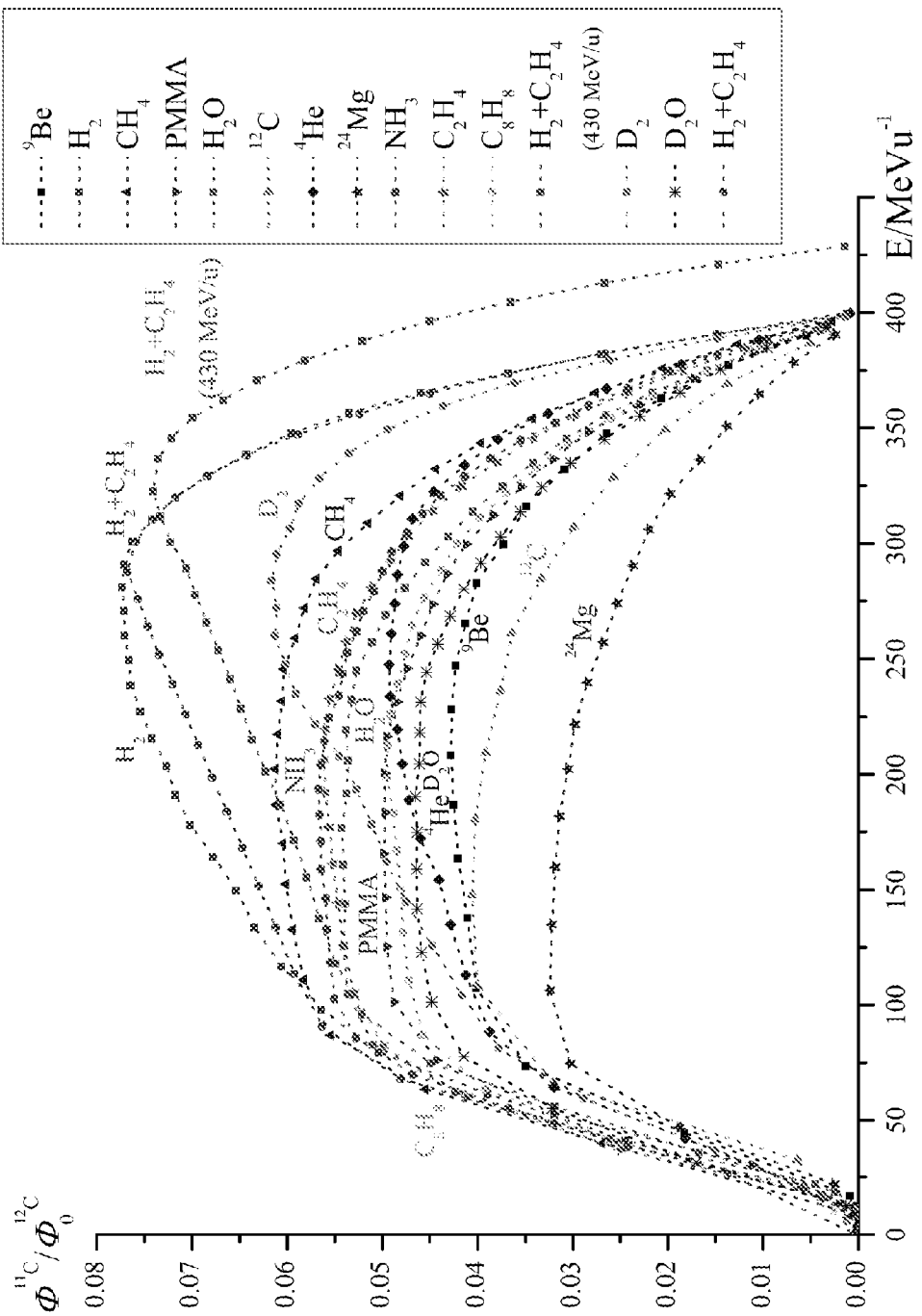
FIGS. 5A and 5B illustrate the fluence of $^{11}C$ ions normalized to the incident $^{12}C$ fluence at the surface as a function of the mean energy of the secondary $^{11}C$ beam (FIG. 5A) and of the corresponding remaining range of the beam in water target decelerator calculated in the slowing down approximation (FIG. 5B). Dotted straight lines are drawn between data points. The combination of an initial liquid hydrogen $^{11}C$ producer and variable $C_2H_4$ decelerators generates a 7-8% fluence of positron emitting $^{11}C$ over most of the ranges (100-350 MeV/u or 5-20 cm).
Figure 5B:
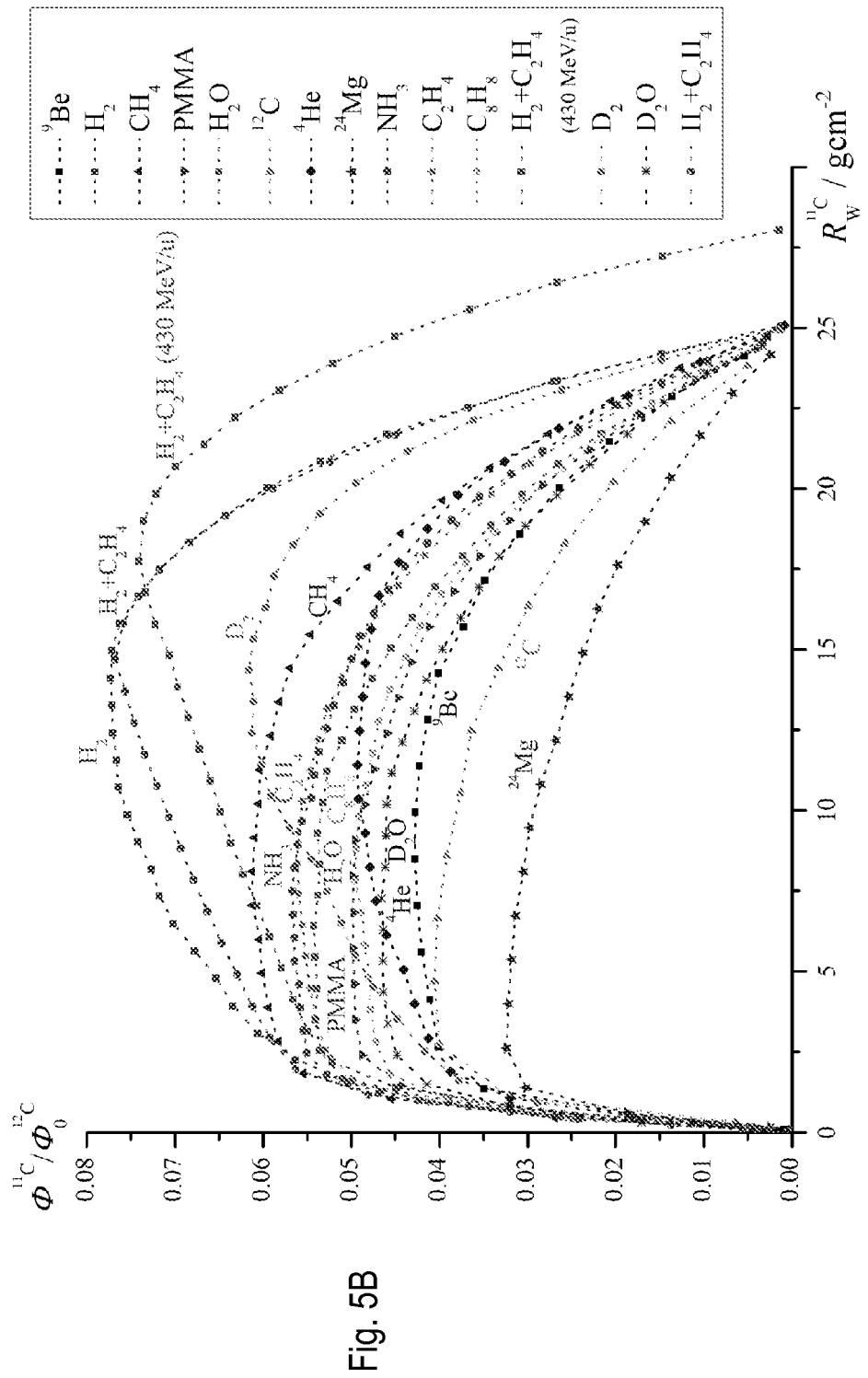

Furthermore, in FIGS. 5A and 5B, the main characteristics of the $^{11}$C secondary beam are shown. In particular, in FIG. 5A the normalized fluence of $^{11}$C ions is shown as a function of the mean energy of the beam, while in FIG. 5B the variation as a function of the remaining range in a water phantom is presented. From a clinical point of view, the last mentioned graph is highly interesting, since it offers a prompt picture of the incident beam fluence available to treat differently located tumor sites in the patient. The range of the $^{11}$C beam has been calculated by using the relation in equation (1) and with values of primary particle ranges in the slowing down approximation evaluated by the Monte Carlo code according to Stopping Power tables in water extracted from the ICRU report 73 and a modified Bethe-Bloch formula.

In the energy region between 100 and 400 MeV/u, the liquid hydrogen exhibits the best characteristics in terms of highest $^{11}$C production. Reversely, for mean energies corresponding to more superficial tumor sites, and ranges lower than 2.4 cm of water equivalent thickness, only few other materials like methane (CH$_4$), water (H$_2$O) or PMMA (C$_5$O$_2$H$_8$) seem to be preferable. However, the difference between the liquid hydrogen curve and the other mentioned materials seem to be almost negligible here.

In fact, the optimal cost effective solution may be using a two component decelerator composed by a first liquid hydrogen part followed by, for example, a polyethylene (C$_2$H$_4$) decelerator. The liquid hydrogen thickness has been chosen in order to approximately correspond to the maximum level of $^{11}$C production. In fact, this solution is preferable than a pure and long liquid hydrogen phantom due to difficulties linked to the quite sophisticated cryogenic system needed in order to keep the liquid lower than 30 K.

However, it may be highly desirable to reach even more deeply located tumors of around 25 cm of depth. In this respect the $^{11}$C production related to a 430 MeV/u of $^{12}$C primary beam was also studied (see FIGS. 5A and 5B) and the results show that a satisfactory level of $^{11}$C production are reached with the dual decelerator.

Moreover, by using hydrogen rich compounds, $^{11}$C ion beam intensity values in the range of about 5-8% of the primary $^{12}$C beam intensity are reached. Consequently, the needed beam intensity for therapy is accomplished by correspondingly increasing the primary beam intensity of about 10-20 times.

The present document clearly shows that sufficiently intense $^{11}$C beams can be produced during the deceleration of a primary $^{12}$C beam. If the intensity of the primary beam could be increased by a factor 10, then similar dose rates of $^{11}$C can be produced as was available with $^{12}$C. With a cyclotron this may be easily feasible by increasing the initial current and conventional doses of $^{11}$C could be produced for example by a combined decelerator and energy and charge selecting system as proposed for the excentric ion gantry disclosed in WO 2005/053794, the teaching of which is hereby incorporated by reference.

It is quite interesting that a first short fixed liquid hydrogen target of about 70 cm or 4.97 g/cm² in length could be combined with a binary system of variable polyethylene degraders. For the remainder of the thickness about 18 g/cm² $C_2H_4$ is required to modulate the $^{11}C$ range from about 20 cm to a few cm with almost the same efficiency (about 95%) as a pure hydrogen decelerator (about 180 cm, cf. FIGS. 3A and 3B) by starting at 400 MeV/u and from about 25 cm starting from 430 MeV/u. This could be done e.g. using the binary decelerator technique with thicknesses of 1, 2, 4, 8, 16, 32, 64, and 128 mm.

Figure 6:
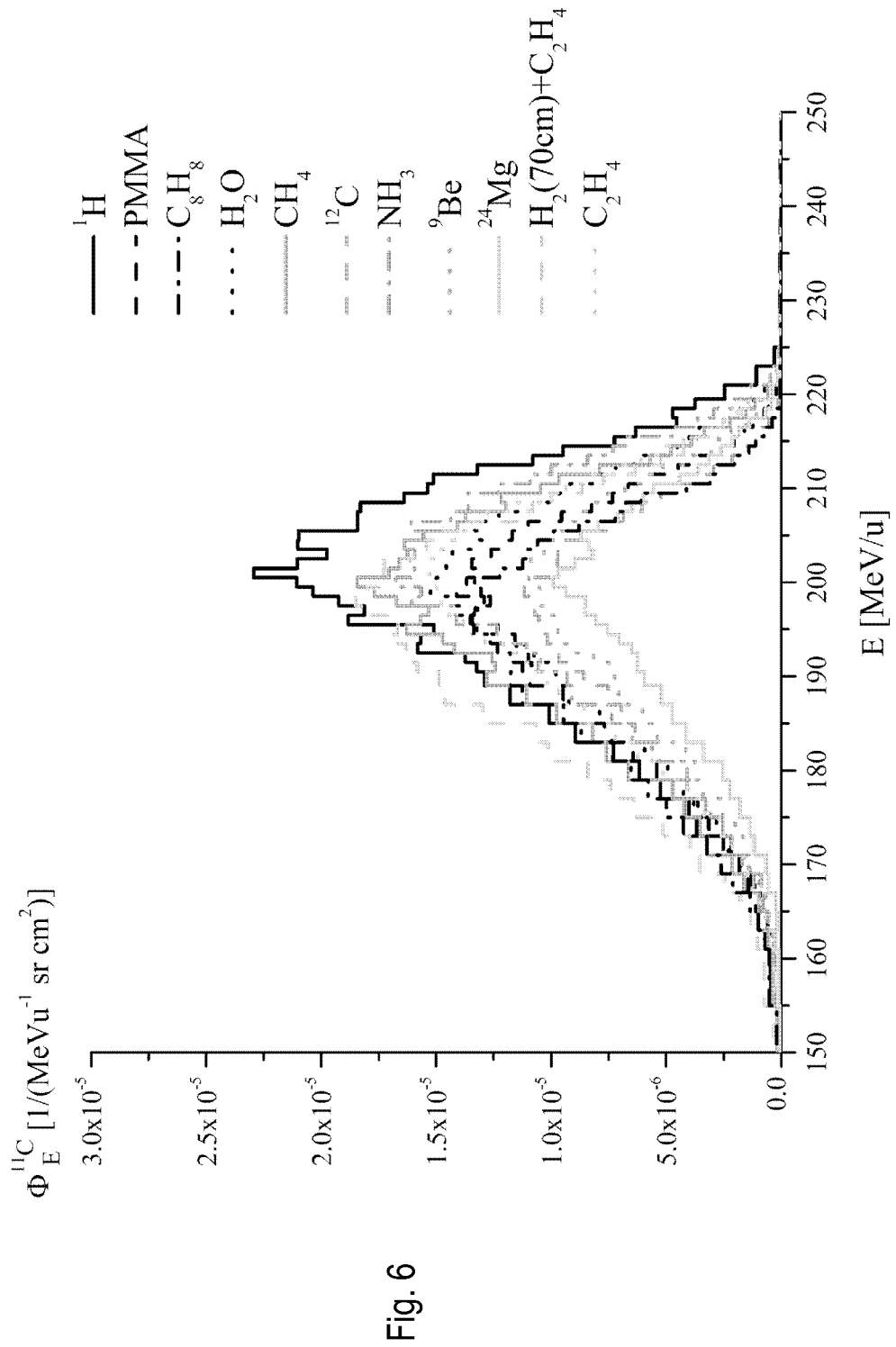
FIG. 6 illustrates fluence differential in energy of the $^{11}C$ ion beams produced in different target materials. Distributions are shown at depths corresponding to a mean energy of the $^{11}C$ ion beam of 200 MeV/u in all the considered materials.
Figure 21:
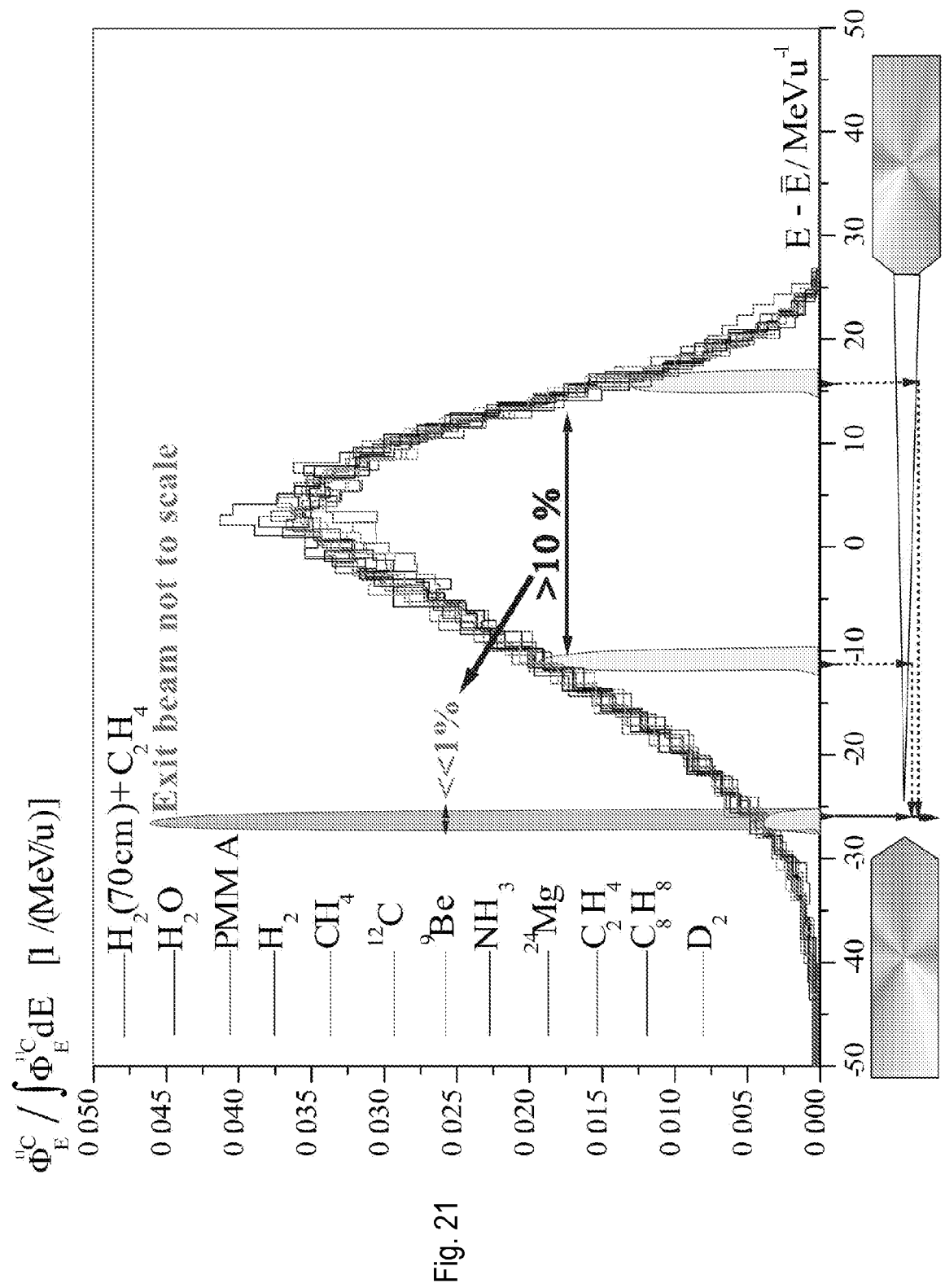
FIG. 21 illustrates a variable wedge filter that can be introduced in the beam line to totally eliminate the energy spread of the $^{11}$C beam placed where the dispersion of the beam is high after the bending magnet. The energy spread curves (FIG. 6) are here shifted by a value corresponding to the mean energy of the distributions and normalized to the integral area below each curve. The thick part of the wedge is on the high energy side so all $^{11}$C ions with different energies leave the optimized variable wedge with one and the same energy to reach the tumor depth with high accuracy. The nonlinear wedge angle can be continuously variable so that it can be adjusted to make the exit $^{11}$C beam monoenergetic independent of which energy and tumor depth that is desired.

It is very clear that hydrogen rich materials are to be preferred both because the $^{11}C$ fluence is the highest and equally important because the multiple scattering is as low as possible, generating a degraded beam with minimal angular spread. However, as seen in FIGS. 6 and 21, the energy spread is almost the same for most light absorbing materials. The optimal efficiency with regard to maximization the high quality $^{11}C$ production is shown in more detail by the resulting energy and angular distributions in FIGS. 6, 8A, 8B and 21.

Furthermore, the $^{11}C$ ions have the interesting property of having a long-enough half life to allow the re-acceleration of the beam once it is produced. In this case, it would be interesting to select the optimal energy of the primary $^{12}C$ beam at which the fluence of $^{11}C$ is as high as possible. This beam then may need re-acceleration (or deceleration) to make ions of any desired energy e.g. by a cyclotron or a linear accelerator.

The main reason for the limited use of radioactive beams in the prior art is their low production rate. However, as disclosed herein it is possible to produce a sufficiently intense $^{11}C$ ion beam with a suitable mean energy to reach even deep sited tumors during the deceleration of an incoming low emittance $^{12}C$ beam provided the target material was carefully selected. The highest fluence build-up of $^{11}C$ fragments is reached in compounds where the fraction by weight of hydrogen atoms is as high as possible. Although a pure liquid hydrogen target is highly desirable, an alternative cost effective two-media combination is also proposed herein. The dual decelerator may be included into an excentric light ion gantry design and could be composed by a first shorter liquid hydrogen section followed by a binary system of variable polyethylene slices to modulate the energy for the PET emitting Bragg peak to reach any desired depth in the patient.

However, to use radioactive beams for treatment it is preferred to also analyze the beam quality describing the emittance of the $^{11}C$ ion beam. In fact, secondary fragments are expected to have increased energy, angular and radial spreads compared to the primary beam and, as a consequence, the limits imposed by the fragment selection system of the accelerator beam line may significantly decrease the yield of fragments.

Herebelow the quality of the $^{11}C$ projectiles produced is assessed in more detail by analyzing their energy spread of variance, as well as their radial and angular variances and covariance. The particle fluences differential in energy, angle and radius has therefore been analyzed for a quite wide range of materials. The overall production efficiency is finally calculated taking into account the finite acceptance of the beam transport system needed to deliver a beam that is suitable for radiation therapy.

Total Distribution Functions of Primaries and Generated Secondary Fragments

The total distribution function of a Gaussian distributed primary light ion beam (e.g. $^{12}C$) in a medium may be described by the product of two terms respectively linked to the solutions of the longitudinal and lateral transport in the medium, which for a rotationally symmetric beams is:

$$\Phi_p(z,r,\theta) = g_p(z) h_p(z,r,\theta) \quad (12)$$

where $g_p(z)$ is longitudinal transport function of primary particles at depth z and $h_p(z,r,\theta)$ is the radial distribution function in the system of coordinates as described for example in the electron report of ICRU-35 where r is the radial distance from the central axis z and $\theta$ is the polar angle of the direction of the motion.

Equation (12) can be expanded in its angular, radial and depth-dependent components and it results in:

$$\Phi_p(z, r, \theta) = \Phi_p(0, 0, 0) \pi^2 \overline{r_p^2}(0) \overline{\theta_{p,c}^2}(0)$$
$$\exp(-\overline{\mu_p}(z) \cdot z) \frac{\exp\left(-\frac{r^2}{\overline{r_p^2}(z)}\right)}{\pi \overline{r_p^2}(z)} \frac{\exp\left(-\frac{(\theta - \overline{\theta_p}(r))^2}{\overline{\theta_{p,c}^2}(z)}\right)}{\pi \overline{\theta_{p,c}^2}(z)} \quad (13)$$

where $\overline{r_p^2}$ is the mean square radius of the primary particles (radial variance) (see equation (17)) and $\overline{\theta_{p,c}^2}$ is the mean square angular spread at the central axis (angular variance) (see equation (24)). $\overline{\theta_{p,c}^2}$ is the most probable angle of motion at the radial distance r and it can be expressed as the ratio between the radial distance r and the distance $s_{p,vir}$ to the point from which the most probable direction of motion seems to emerge, the so called virtual point source. $\overline{\mu_p}$ is the mean value of the associated attenuation coefficient of the primary ions. This physical quantity is related to the mean nuclear interaction cross section and, in first approximation at high energies, its energy dependence may be disregarded. Moreover, the fluence of primary particles in the limit when z, r and $\theta$ approach zero is described by the first five factors in the formula. The closely exponential attenuation of the incoming primary beam in the medium is taken into consideration by the first exponential term in the formula, while the last two exponentials describe respectively the radial and angular distribution of the beam at a depth z in the material.

In the present case, this formula can be used to describe the primary $^{12}C$ beam at a certain depth z in the decelerator material very accurately, and to some extent also the newly produced $^{11}C$ beam at a certain depth in the patient body, once extracted from the beam line optics and thus purified from other contaminating fragments.

The secondary heavy fragments generated at different depths s during the attenuation of the primary beam in the medium may be expressed by a modified version of the equation (12). This is the case, for instance, if $^{11}C$ fragments generated in the decelerator before enter the beam line. The fluence of fragments of a certain kind i can thus be described by the following analytical formula:

$$\Phi_i(z, r, \theta) = -\int_0^{min(z,R_p)} C_i \frac{d\Phi_p(s)}{ds}$$
$$e^{-\mu_i(z-s)} \overline{r_i^2}(0,0) \overline{\theta_{i,c}^2}(0,0) \frac{e^{-\frac{r^2}{\overline{r_i^2}(z,s)}}}{\overline{r_i^2}(z,s)} \frac{e^{-\frac{(\theta-\overline{\theta_{i,r}})^2}{\overline{\theta_{i,c}^2}(z,s)}}}{\overline{\theta_{i,c}^2}(z,s)} ds \quad (14)$$

where $R_p$ is the practical range of primary particles, $\overline{r_i^2}$ is the mean square radius of the fragments, $\overline{\theta_{i,c}^2}$ is their mean square angular spread at the central axis and $\overline{\theta_{i,c}^2}$ is the most probable angle of motion of the considered fragments at the radial distance r. The term $$C_i \frac{d\Phi_p(s)}{ds}$$

describes the simultaneous loss of primary fragments and the consequent build-up of secondary fragments. Fragments of type i are in fact produced in a certain fraction $C_i$ with respect to all the other fragments that might be possibly generated in the interaction between the incoming ions and the target nuclei. In fact, $$C_i \frac{d\Phi_p(s)}{ds}$$

may be also expressed as:

$$C_i \frac{d\Phi_p(s)}{ds} = n\sigma_i \exp(-n\sigma_{r,0} s) \quad (15)$$

where $\sigma_i$ is single channel reaction cross section, $\sigma_{r,0}$ is the total reaction cross section and n the number of atoms per unit of volume.

Furthermore, similarly to equation (13), the first exponential accounts for the attenuation of generated secondaries, where the mass attenuation coefficient of primary particles is now replaced with that applicable for the considered fragments. However, in the case of $^{11}C$ fragments, the value of the mass attenuation coefficient is very close to the one for the primary $^{12}C$ ions.

Angular Spread

In most cases, it is also of interest to describe the pure depth-dependent angular distribution irrespective of its radial dependence r. In the case of primary particles, this may be obtained by integrating the total fluence distribution described by equation (12) over all the radii:

$$\Phi_p(z, r) = \Phi_p(0, 0) \overline{r_p^2(0)} \exp[-\overline{\mu}_p(z)z] \frac{\exp\left(-\frac{r^2}{r_p^2(z)}\right)}{r_p^2(z)} \quad (16)$$

with the mean square angular spread of primary ions given by:

$$\overline{\theta_p^2(z)} = \overline{\theta_p^2(0)} + \int_0^z T_p[E_p(u)] du \quad (17)$$

$T_p$ is the mass scattering power of the primary particles penetrating the target material (in this case $^{12}C$ ions) and it describes the increment of the mean square angle of divergence per unit distance traveled. The mass scattering power is calculated for the energy $E_p$ that corresponds to the depth u along the z axis. In the case of light ions, a modified version of the depth dependent mass scattering power first derived for electron in the ICRU-35 is very useful:

$$\frac{T}{\rho} = \frac{1}{\rho} \frac{d\overline{\theta^2}}{dl} \quad (18)$$

$$= \frac{4\pi N_A}{M_A} \left(\frac{m_e r_e Z_{p,eff} Z_A}{(1+\tau)\beta^2 M_p}\right)^2$$

$$\left[\ln\left(\left(\frac{\theta_m}{\theta_\mu}\right)^2 + 1\right) + \left(\left(\frac{\theta_m}{\theta_\mu}\right)^2 + 1\right)^{-1} - 1\right]$$

where $N_A$ is the Avogadro's number, $r_e$ is the classical electron radius, $M_e$ is the electron mass, $M_p$ is the mass of the primary ion, $\tau$ is the ratio between the kinetic and the energy at rest of the projectile ion, $\beta$ is the velocity of the incoming ion normalized to the speed of light and $\theta_\mu$ is the screening angle due to the screening of the nucleus by orbital electrons and $\theta_m$ is the cut-off angle due to the finite size of the nucleus. For a given velocity, the mass scattering power is related to the type of incoming ion trough its effective charge $Z_{p,eff}$. In case of light ions, $Z_{p,eff}$ may be simply approximated with the charge $Z_p$ except for the deepest penetration beyond the Bragg peak.

The screening angle $\theta_\mu$ may be expressed as the ratio between the reduced De Broglie wave length of the incident particle $\lambda$ and the atomic radius $r_a$, according to:

$$\theta_\mu = \frac{\lambda}{r_a} = \frac{\alpha Z_p^{1/3}}{\beta(1+\tau)} \frac{m_e}{M_p} \frac{1}{0.88534} \quad (19)$$

where $\alpha$ is the fine-structure constant.

Similarly, the cut-off angle $\Theta_m$ may be expressed as the ratio between the reduced De Broglie wave length of the incident particle $\lambda$ and the radius of the nucleus $r_n$:

$$\theta_m = \frac{\lambda}{r_n} = \frac{1}{0.49} \frac{A_p^{-1/3}}{\alpha\beta(1+\tau)} \frac{m_e}{M_p} \quad (20)$$

where $A_p$ is the mass number of the incoming projectile.

Furthermore, in equation (18) the parameters that describe the dependence of the mass scattering power on decelerator material are the molar mass $M_A$ and the atomic number $Z_A$. For light materials, it is often possible to approximate the numerical value of $M_A$ by $2Z_A$, with the only exception of protons where $M_A \approx Z_A$. From these considerations, it is then expected that, for a given projectile and velocity, media having lower $(Z_A)^2/M_A$ deflect the particle trajectory less than others. Thus, in case of an incoming $^{12}C$ ion beam of a fixed energy per nucleon, the mass scattering power is the lowest in the hydrogen case. As a consequence, it is also expected that the radial variance is as low as possible in the case of hydrogen compared to other light materials, if the same depth in the material is considered. In analogy with the procedure previously described for primary ions, the depth-dependent angular distribution for the i-fragments results in:

$$\Phi_i(z, \theta) = \quad (21)$$

$$-\int_0^z C_i \overline{\theta_i^2}(0,0) \frac{d\Phi_p(s)}{ds} \exp[-\overline{\mu}_i(z-s)] \frac{\exp\left(-\frac{\theta^2}{\theta_i^2(z,s)}\right)}{\theta_i^2(z,s)} ds$$

where:

$$\overline{\theta_i^2(z,s)} = \overline{\theta_p^2(s)} + \overline{\theta_i^2(s)} + \int_s^z T_i[E_i(u)] du \quad (22)$$

This expression can be simplified by more explicitly considering the transport of the primaries (see equation (17)):

$$\overline{\theta_i^2}(z,s) = \overline{\theta_p^2}(s) + \overline{\theta_i^2}(s) + \int_s^z [T_i(u) - T_p(u)] du \quad (23)$$

Radial Spread

In analogy with the previous section, by integrating equation (13) in the whole angular interval, the purely spatial distribution may be obtained:

$$\Phi_p(z, r) = \Phi_p(0, 0)\overline{r_p^2}(0)\exp[-\overline{\mu}_p(z)z] \frac{\exp\left(-\frac{r^2}{\overline{r_p^2}(z)}\right)}{\overline{r_p^2}(z)} \quad (24)$$

The mean square radius at depth z is related both to the beam geometry and to the properties of the medium and is given by the following equation:

$$\overline{r_p^2}(z) = \overline{r_p^2}(0) + 2\overline{r\theta_p}(0)z + \overline{\theta_p^2}(0)z^2 + \int_0^z (z-u)^2 T_p(E_p(u)) du \quad (25)$$

where $\overline{r_p^2}(0)$, $\overline{\theta_p^2}(0)$, $\overline{r\theta_p}(0)$ are respectively the mean square radial square, the mean square angular spread and covariance at the surface of the primary incident beam.

In analogy with the procedure previously described for primary ions, the depth-dependent radial distribution for the i-fragments results in:

$$\Phi_i(z, r) = -\int_0^{\min(z, R_p)} C_i \overline{r_i^2}(0, 0) \frac{d\Phi_p(s)}{ds} e^{-\mu_i(z-s)} \frac{e^{-\frac{r^2}{\overline{r_i^2}(z,s)}}}{\overline{r_i^2}(z, s)} ds. \quad (26)$$

with the mean radial variance given by:

$$\overline{r_i^2}(z, s) = \overline{r_p^2}(s) + (2\overline{r\theta_p}(s))(z-s) + (\overline{\theta_p^2}(s) + \overline{\theta_i^2}(s))(z-s)^2 + \int_s^z (z-u)^2 T_i(E_i(u)) du \quad (27)$$

Similarly to equation (23), the expression described in equation (27) can be modified by including a more explicit dependence on the mass scattering of the primary particles:

$$\overline{r_i^2}(z, s) = \overline{r_p^2}(z) + \overline{\theta_i^2}(s)(z-s)^2 + \int_s^z (z-u)^2 [T_i(u) - T_p(u)] du \quad (28)$$

Covariance of the Radial and Angular Spread

The mean covariance of the radial and angular spread describes the increase in the most probable inclination of the particles of the beam at increasing off-axis positions. The mean covariance at depth z in case of primary particles is given by the following equation:

$$\overline{r\theta_p}(z) = \overline{r\theta_p}(0) + \overline{\theta_p^2}(0)z + \int_0^z (z-u) T_p[E_p(z-u)] du \quad (29)$$

In analogy with the previous cases, a similar expression can be derived for fragment i:

$$\overline{r\theta_i}(z,s) = \overline{r\theta_p}(z) + \overline{r\theta_i^2}(s)(z-s) + \int_s^z (z-u)[T_i(u) - T_p(u)] du \quad (30)$$

which more explicitly show how the multiple scatter is switched off from p to i beyond s.

Energy Spread

The energy loss of an incoming particle penetrating a medium is a statistical process. The amount of energy loss in each individual interaction is a local value characterized by a Gaussian like probability distribution around a mean energy loss value.

Generally, an incoming ion undergoes a certain number of single collision events during its penetration path in the medium and the corresponding energy loss distribution might be described with a binomial function. Alternatively, a Landau or more accurately a Vavilov distribution function might also be used to describe the process. The Vavilov distribution is a skewed Gaussian like distribution that varies depending on the incoming ion energy and the depth of penetration. However, due to the central limit value theorem, when the number of randomly distributed collisions becomes high, for instance, when the pathlength increases, the Vavilov distribution can be rather well-approximated by a pure Gaussian function.

A particle of energy $E_0$ that penetrates a path length z has a certain probability of losing an energy $\Delta$ described by the following Gaussian distribution function:

$$F(\Delta, z) = \frac{1}{\sqrt{2\pi\sigma_E^2}} \exp\left(-\frac{(\Delta - \Delta_{av})^2}{2\sigma_E^2}\right) \quad (31)$$

where $\Delta_{av}$ is the mean energy loss value and $\sigma_E$ is the standard deviation of the Gaussian distribution function. The corresponding variance $\sigma_E^2$ is given by:

$$\sigma_E^2 = \frac{4\pi r_E^2 (m_e c^2) N_A Z_A Z_p^2}{(1-\beta^2) M_A} \left[1 + 2\left(\frac{m_e}{M_0}\right)(1-\beta^2) + \left(\frac{m_e}{M_0}\right)^2\right]^{-1} \quad (32)$$

The formula above shows that, for a certain projectile and velocity, materials having lower $Z_A/M_A$ ratio are expected to produce a lower energy straggling. Thus, the energy straggling of a primary $^{12}C$ ion beam in hydrogen ($Z_A/M_A=1$) is the highest compared to other light materials. So from an energy spread point of view a high atomic number decelerator produce less energy spread and is more advantageous.

The description of the whole energy spread in case of secondaries is far more complex than in the primary ion case. The energy distribution of fragments at a certain depth in the material is due to the simultaneous interaction of many different physical factors. It is in fact not only affected by the energy straggling of the fragments themselves, but also by the energy straggling of the primary ions that generate them. Moreover, the energy distribution function is also widened by the fact that secondary fragments are produced at different depths in the material by incoming ions already having then different energy straggling values. As a consequence, the energy spread of secondary fragments is expected to be much higher than for the primary ions as shown in FIG. 6.

SHIELD-HIT Code and Irradiation Conditions

In the present study, Monte Carlo simulations were performed with the SHIELD-HIT+ code. The SHIELD-HIT code allows simulating the interactions of hadrons and nuclei of arbitrary mass and charge transported in macroscopic targets. The energy range covered by the code goes from 25 KeV/u up to 2 GeV/u. The lower energy limit can be extended to 1 KeV/u by using a modified Bethe and Bloch formula. Neutrons are transported down to thermal energies.

The nuclear inelastic interactions are based on the Many Stage Dynamical Model, while the elastic scattering is handled by using simple diffraction like formulas.

In SHIELD-HIT07 the energy loss of particles is taken into account by the Gaussian or Vavilov energy straggling models, while the multiple scattering is described by the Gaussian model. The choice of the appropriate energy loss model to be used in the simulations is left to the user. In our case, calculations have been performed by using Gaussian distribution functions. However, no significant differences are noticed by using the more complex Vavilov alternative. Furthermore, the present version of the code provides also a double differential scoring of the particle fluences in energy and angle of both primary ions and the produced fragments.

Calculations were performed by simulating the interaction of an incoming $^{12}$C beam of a fixed initial energy of 400 MeV/u orthogonally impinging on the axis of a cylindrical target of 10 cm of radius. Track length fluences differential in energy and angle of produced $^{11}$C fragments were scored in 1 mm thick slices. Particle fluences differential in the radius were scored in concentric slices having 0.5 mm of radial increment up to 10 cm.

The target materials considered in the study were: water ($H_2O$), PMMA ($C_5O_2H_8$), beryllium ($^9$Be), graphite ($^{12}$C), liquid hydrogen ($H_2$), liquid methane ($CH_4$), aluminium ($^{13}$Al), magnesium ($^{12}$Mg), liquid ammonia ($NH_3$), polystyrene ($C_8H_8$) and polyethylene ($C_2H_4$). In addition, a two media target made of a first liquid hydrogen section of variable length (from 20 to 70 cm) followed by a polyethylene section was also studied.

In order to appropriately compare the characteristics of the energy, angular, radial distributions of $^{11}$C fragments in the different target materials, the depths in the targets were selected in order to have an approximately equal mean energy value of the $^{11}$C fragments for all the materials. Results are shown for a mean energy of the secondary $^{11}$C ion beam of about 200 MeV/u.

Statistical Analysis

In order to conduct a more careful study of the energy, angular and radial distribution functions for the different materials considered in the work, a statistical analysis of the Monte Carlo results was performed. The statistical analysis included calculation of the first four moments of the energy distributions: the mean energy (momentum of order I), the variance $\sigma^2$ (momentum of order II), the skewness (momentum of order III) and the kurtosis (momentum of order IV).

For simplicity, in this section the statistical parameters are referred to the energy distribution function $\Phi_E$ of generated secondary $^{11}$C fragments. However, the same analysis can be applied to an arbitrary distribution function (e.g. angular distribution, radial distribution etc.).

The mean value of the energy distribution function is defined by:

$$\bar{E} = \frac{\int_0^\infty E \Phi_E dE}{\int_0^\infty \Phi_E dE} \tag{33}$$

where $\Phi_E$ is the fluence differential in energy of the considered particles.

The variance of the distribution is:

$$\sigma^2 = \frac{\int_0^\infty (E - \bar{E})^2 \Phi_E dE}{\int_0^\infty \Phi_E dE} \tag{34}$$

Furthermore, the momentum of order III or skewness (S) is also considered. This index is a measure of the degree of departure from a symmetric distribution. A distribution is said to be positively skewed if its tail is extended in the positive direction, while it is vice versa negatively skewed if its tail is higher in the negative direction. The skewness for a normal distribution is 0.

$$S = \frac{\sqrt[3]{\int_0^\infty (E - \bar{E})^3 \Phi_E dE}}{\sigma^3 \int_0^\infty \Phi_E dE} \tag{35}$$

The kurtosis (K) is an index of the degree of peakedness of a distribution with respect to a normal distribution. A normal distribution has the kurtosis value equal to 3. If the kurtosis is higher than 3, the considered distribution is more peaked than a Gaussian function.

$$K = \frac{\sqrt[4]{\int_0^\infty (E - \bar{E})^4 \Phi_E dE}}{\sigma^4 \int_0^\infty \Phi_E dE} \tag{36}$$

Furthermore, it is of interest in this study to evaluate the energy distribution functions of $^{11}$C fragments produced in different materials, the resulting values of the calculated momentum are described as a function of the molar mass of the material considered. In case of compounds, an effective molar mass is calculated.

Comparisons of Different Materials

As mentioned in the previous section, to properly compare the characteristics of the secondary $^{11}$C ion beam mainly produced by projectile fragmentation of the primary $^{12}$C ion beam in the different decelerator materials, the analysis of energy, angular and radial beam spread is conducted at a depth in each target material corresponding to the $^{11}$C beam mean energy of about 200 MeV/u. Since the ultimate goal of the present study is to produce a positron emitter beam that could be used to directly treat patients, it is in fact of importance to compare the characteristics of the generated $^{11}$C beam at a given energy corresponding to a given tumor depth.

In FIG. 6, the fluence differential in energy of the $^{11}$C fragments is shown for different materials composing the decelerator. The $^{11}$C ion beam production is high in materials having high fraction by weight of hydrogen atoms. This is demonstrated by the area below the distributions shown in FIG. 6, where it is clearly seen that the pure liquid hydrogen always produces the highest values. However, the shape of the distributions as well as their spread is comparable in all the shown cases. These characteristics are more evident in FIG. 21 where the curves of the $^{11}$C ion fluences differential in energy are slightly shifted to a value corresponding to the mean energy of each distribution and the area below each distribution is normalized to unity. In fact, the energy distribution curves are almost perfectly superimposed, except for the random variation in peak heights.

Figure 7:
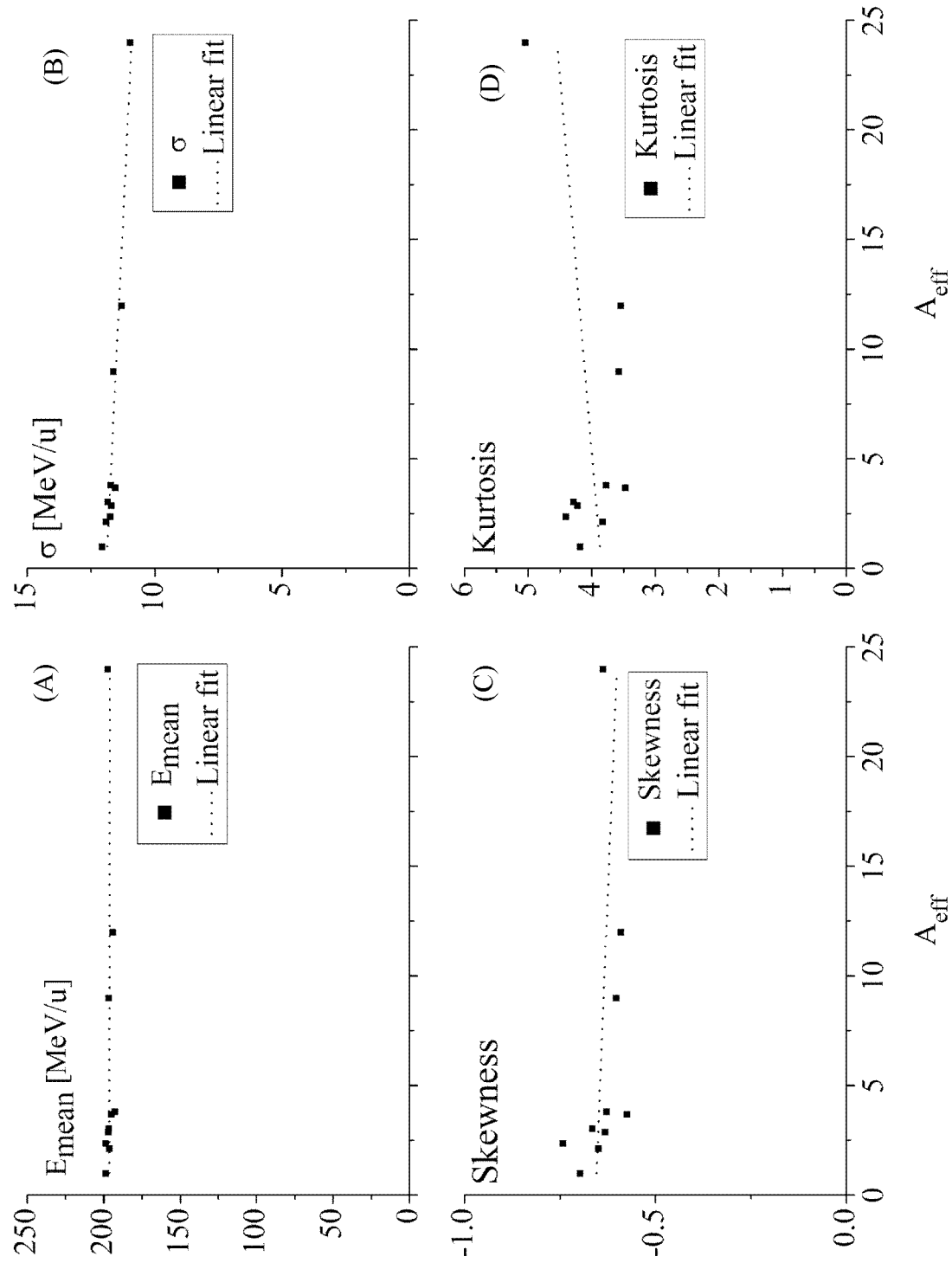
FIGS. 7A to 7D illustrate statistical analysis of the energy distribution curves of $^{11}C$ ions generated trough fragmentation of a primary $^{12}C$ ion beam in several target materials. Mean energy values of the distributions (FIG. 7A), standard deviations (FIG. 7B), skewness (FIG. 7C) and kurtosis (FIG. 7D) values are presented as a function of the mass number of the target materials.

The outcome of the statistical analysis conducted on the $^{11}$C ion beam energy distribution curves is presented in FIG. 7. Mean energy values, standard deviations of the distributions as well as skewness and kurtosis values are shown as a function of the effective molar mass of the considered target materials. As expected, the mean energy values of the $^{11}$C fragments are rather closely distributed around 200 MeV/u. The calculated standard deviation of the distributions is slightly decreasing with the increasing of the mass number of the target material of the decelerator. Since the mean energy values of the curves are rather constant, this is an indication that the heavier target materials considered in this study have a slightly lower energy spread at depths corresponding to the same mean energy of produced $^{11}$C fragments. The difference is however minimal and it may not be inferred from the graphs shown in FIG. 7. As expected from the observation of the shape of the $^{11}$C energy distributions, the skewness shows in all the considered cases negative values indicating distribution tails primarily shifted towards energies lower than the mean energy values. Skewness values seem to be rather constant for the materials having mass number higher than 5, while in all the other cases the distribution of values is more spread out. A similar spread is also found in light materials for the case of the kurtosis. However, at larger masses the kurtosis shows a value that increases slowly as a result of the highest peak value shown in the energy distribution of FIG. 21. In general, the shown energy spread curves have values higher than 3 indicating a curve shape more peaked than a normal distribution.

Figure 8A:
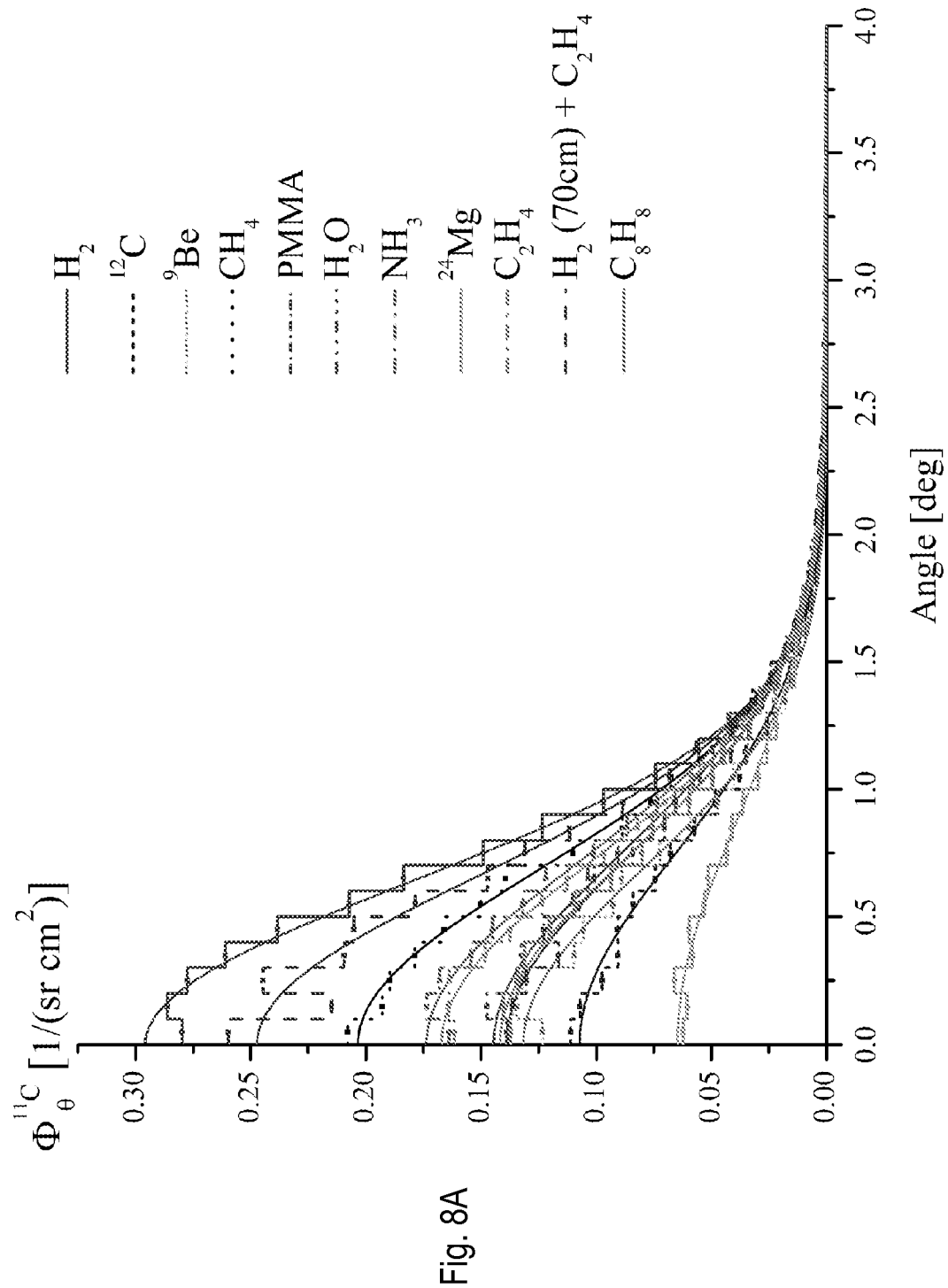
FIGS. 8A and 8B illustrate curves of the fluence differential in angle of the $^{11}C$ ion beam generated by the fragmentation of a primary $^{12}C$ ion beam in different target materials and fitted with Gaussian functions (FIG. 8A) and Gaussian fitting functions normalized to the peak values of the angular distribution curves (FIG. 8B). All presented curves are calculated at depths in the target materials corresponding to a mean energy of the $^{11}C$ ion beam of 200 MeV/u.
Figure 8B:
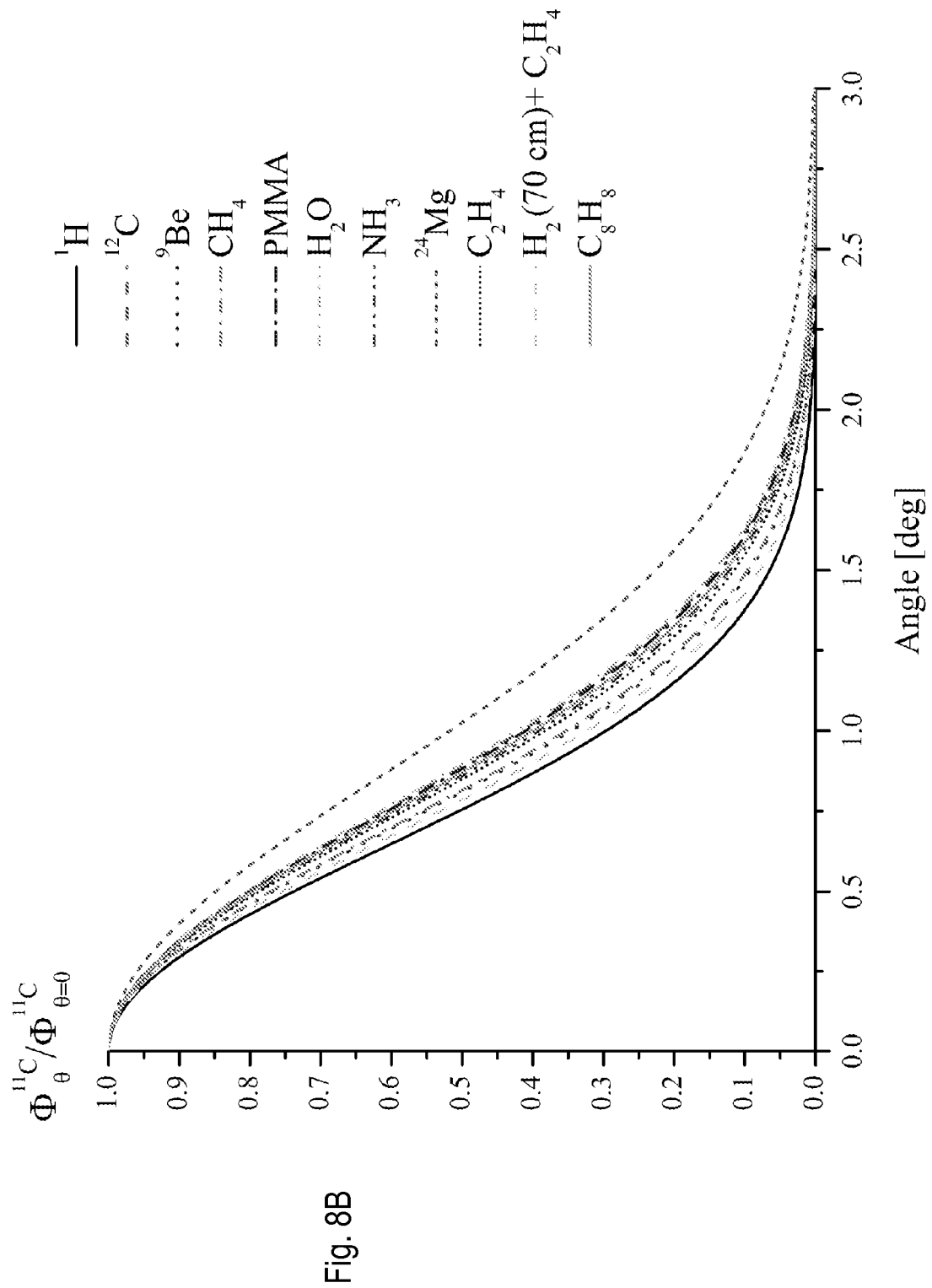

FIGS. 8A and 8B show the fluences differential in angle of the $^{11}$C ion beam generated in the considered targets. In FIG. 8A the distributions calculated by the Monte Carlo code are fitted with a Gaussian functions. In FIG. 8B, the Gaussian fitting curves are normalized to the value of the distributions at θ=0. The angular spread is the result of the synergic effect of the multiple scattering of the primary $^{12}$C beam and generated $^{11}$C fragments, as discussed in section Angular spread. The multiple scattering is smaller if the considered particle beam penetrates materials having lower ratio of $Z_A^2/M_A$. In the range of elemental materials considered in this study, the lowest ratio corresponds to the pure liquid hydrogen target. Shown results confirm the theoretical predictions giving a larger angular spread in case of heavier materials.

Figure 9:
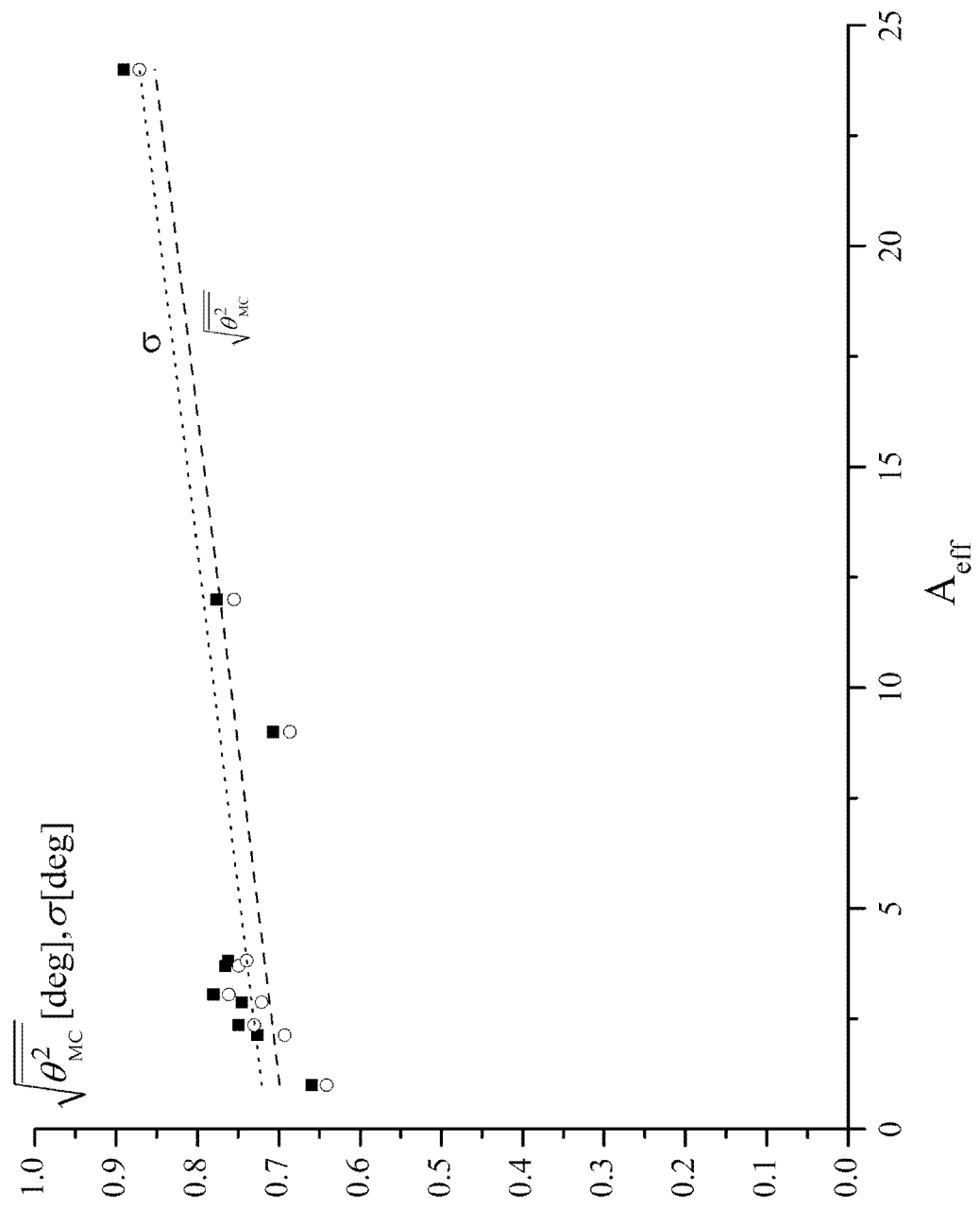
FIG. 9 illustrates statistical analysis of the angular distribution curves of $^{11}C$ ions generated trough fragmentation of a primary $^{12}C$ ion beam in several target materials. Square root of the mean angular square values of the Monte Carlo calculations shown in FIG. 8A and standard deviations of the angular distributions resulting from Gaussian fitting functions shown in FIG. 8B as a function of the mass numbers of the materials.

The general increase of the angular spread for increasing values of the effective atomic mass of the materials is further confirmed by the calculations shown in FIG. 9, where the square root of the mean angular spread values of the Monte Carlo calculations and the standard deviations of Gaussian fitting functions of the angular distributions are presented. The two sets of data points are fitted with linear functions. The shift between the two resulting linear functions is probably due to different weighting of the statistical noise of the Monte Carlo simulations.

Figure 10:
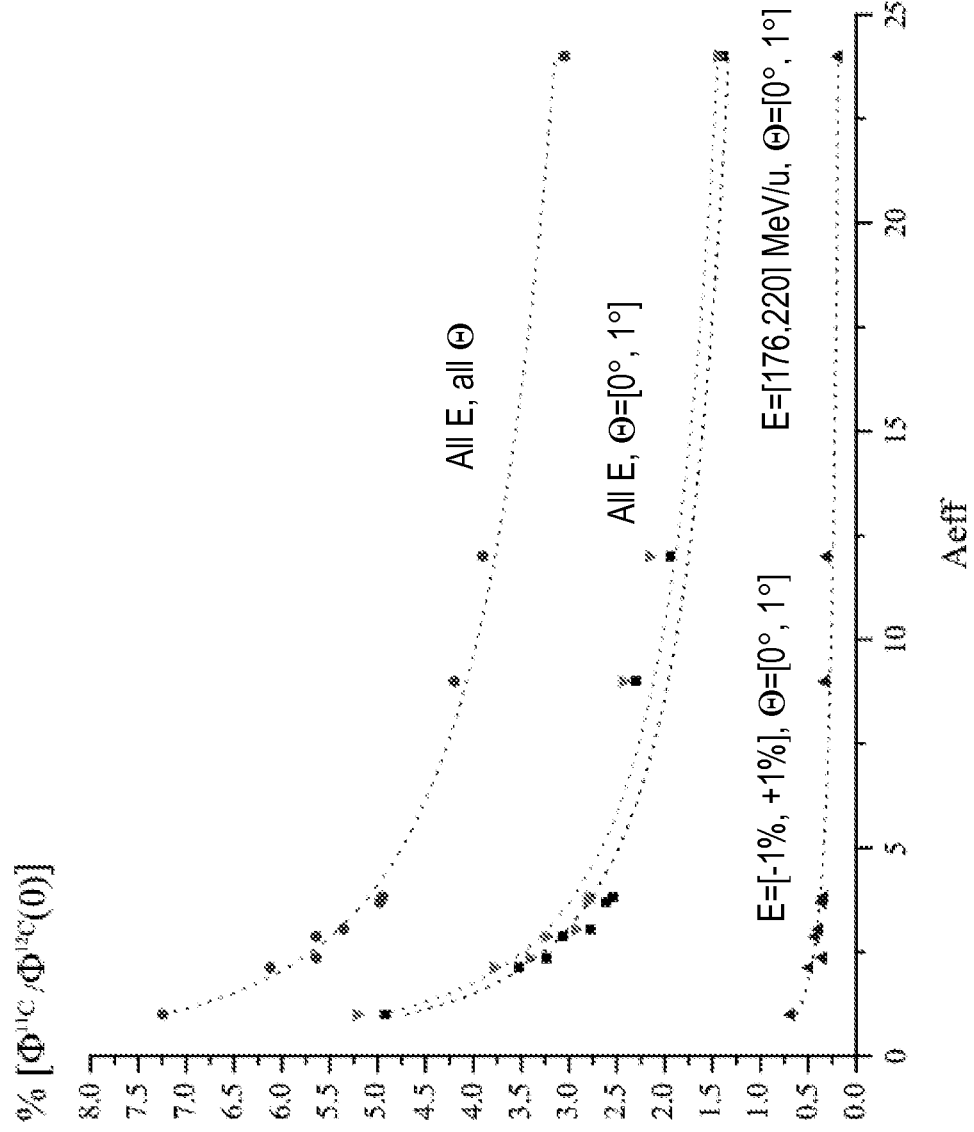
FIG. 10 illustrates analysis of the produced $^{11}C$ fragment fluences normalized to the incoming fluence of primary $^{12}C$ ions as a function of different acceptance limits in the angle and energy spreads. Results corresponding to the different materials are plotted as a function of the mass number of the considered targets. The data set indicated with full circles corresponds to the $^{11}C$ ion production when all the energies and angles are allowed. Full reversed triangles indicate the $^{11}C$ fluence in correspondence of all the energies and for angular values limited to 1 degree of aperture, while full squares correspond to an energy spread in the range of 176-220 MeV/u and the angular limit of 1 degree. Finally, full triangles represent the percentage of $^{11}C$ ion production for an energy spread limited to ±1% of the mean energy value and an angular limit of 1 degree. All the data sets are fitted with exponential functions indicated as dashed lines in the figure.

Furthermore, the production efficiency of the $^{11}$C ion beam as a function of the mass number of the different targets is studied for different combinations of angular or energy intervals (FIG. 10). Full circles in the figure represent the dataset corresponding to the $^{11}$C fragments for which no limitation in energy and angle is applied. In this case, the production efficiency of the $^{11}$C ion beam ranges from about the 7.25% reached in case of a pure liquid hydrogen target to values lower than about the 3% for a magnesium target. However, almost 2% of the production efficiency is lost if the angular spread is limited to 1 degree with an unlimited energy range (full triangles) or an energy range from 176 to 220 MeV/u (full squares). Furthermore, if the $^{11}$C ion energy distribution is limited to values corresponding to ±1% of the mean energy value (about 200 MeV/u in all the cases) and the permitted angular range is set to 1 degree, the production efficiency notably drops to values below the 1% for all the considered materials. Even if the angular spread is no major problem it is preferred to reduce the energy spread.

Figure 11:
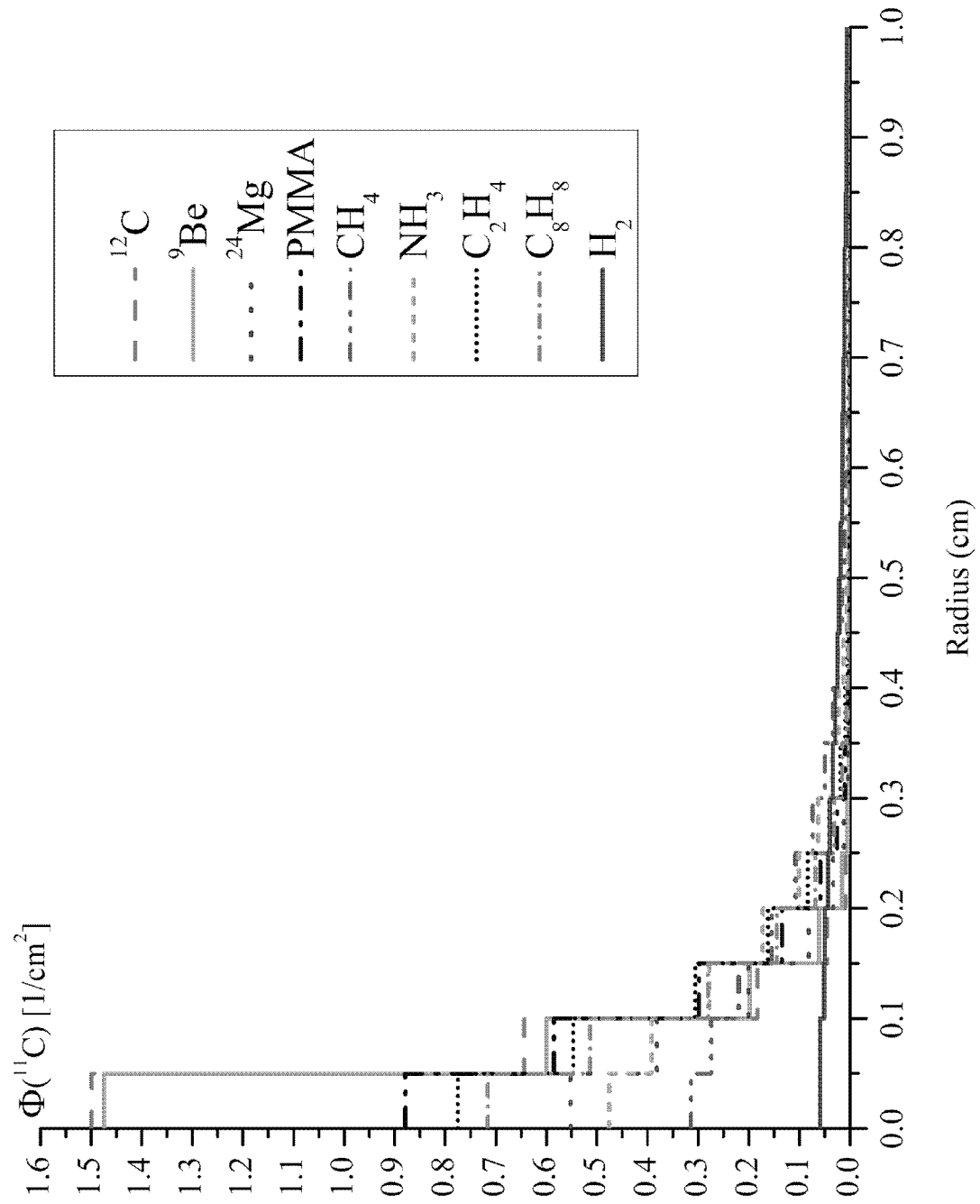
FIG. 11 illustrates radial spread distributions of the $^{11}C$ ion beam generated by fragmentation of $^{12}C$ primary ion beam in different target materials. Distributions are shown at depths corresponding to a mean energy of the $^{11}C$ ion beam of 200 MeV/u in all the considered materials. Due to the low density of a pure liquid hydrogen target, the effective beam spot size is quite large.

FIG. 11 illustrates the radial spread of the $^{11}$C fragments in the different materials composing the decelerator. The fluences differential in radius of the $^{11}$C ions are calculated as track lengths divided by the volumes of the radial slices having 0.5 mm of radial increment. The mentioned volumes in which the track lengths are scored increase as the distance from the central axis of the cylinder increases. As a consequence, even if a high number of fragments is present in the peripheral area of the radial slice their contribution seems to be reduced in comparison with the fluences calculated for smaller radii.

From these calculations it is seen that the $^{11}$C fragments generated in a pure liquid hydrogen target are more spread out than in other materials. This is due to the fact that the characteristics of the produced $^{11}$C ion beam are compared for a fixed mean energy of about 200 MeV/u. In fact, in order to decelerate the beam to such a mean energy value the portion of liquid hydrogen that the $^{11}$C ion beam has to penetrate is much longer than in the other cases (almost 123 cm of liquid hydrogen). It then results that, even if the multiple scattering in the mentioned material is the lowest and the angular spread describing the direction of motion of the fragments is the narrowest, the radial distribution is the largest.

Comparisons of Liquid Hydrogen Decelerators of Variable Length

As was discussed in the foregoing, from the point of view of the total $^{11}$C fragment production efficiency and angular distribution spread, a pure liquid hydrogen decelerator seems to be the most appealing solution. Unfortunately, this material also shows the highest radial spread of the effective source. Therefore, being the energy spread almost comparable for all the materials, an alternative solution resulting in a good compromise between the radial spread of $^{11}$C fragments and their production yield might be a decelerator made of a combination of two materials: a first liquid hydrogen section followed by polyethylene. In this section, the characteristics of a dual decelerator are studied with a variable length of the first liquid hydrogen section from 20 to 70 cm.

Figure 12:
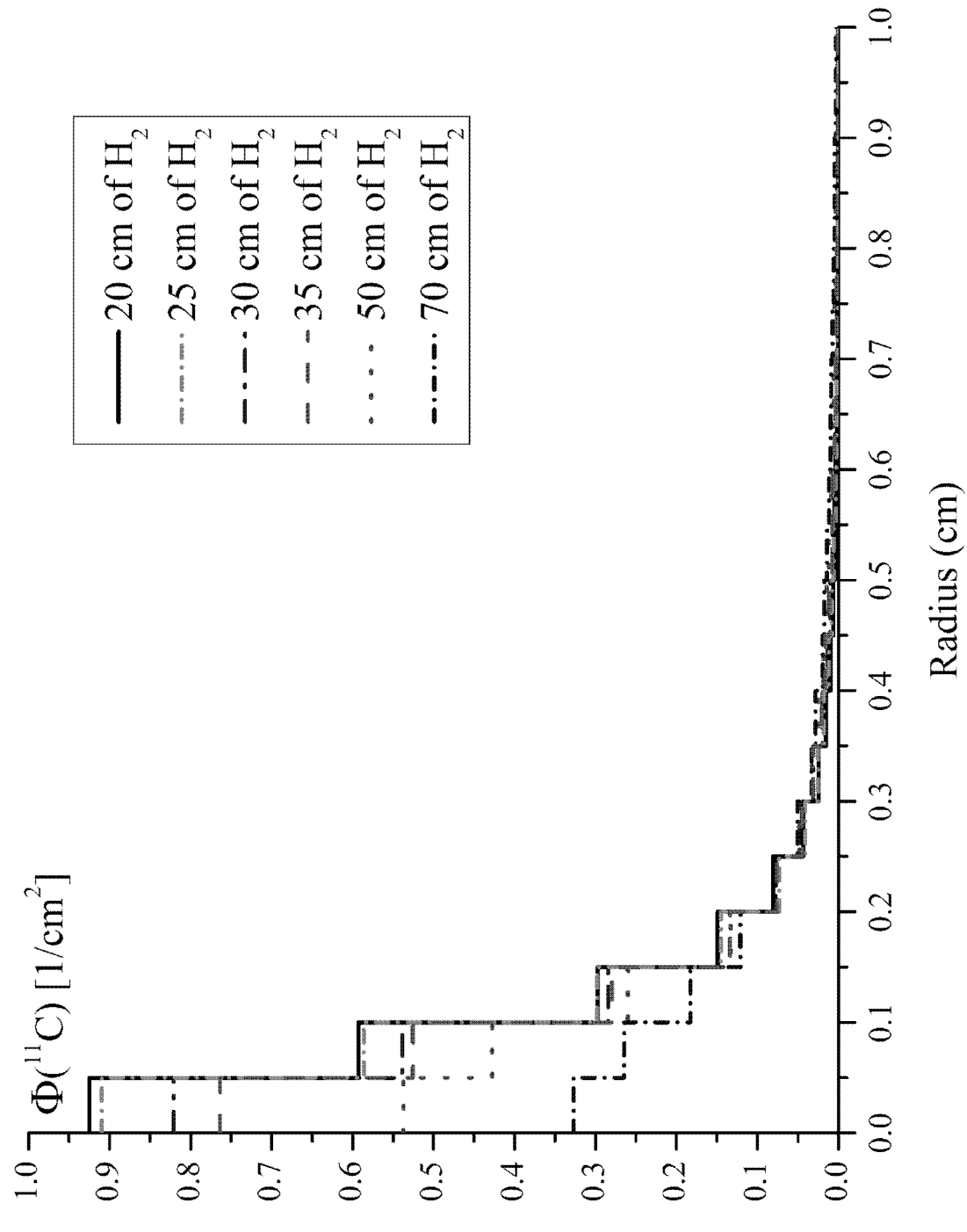
FIG. 12 illustrates radial spread distributions of the $^{11}C$ ion beam generated by fragmentation of $^{12}C$ primary ion beam in a decelerator made of a first section of liquid hydrogen of variable length (from 20 to 70 cm) and the remaining part of polyethylene ($C_2H_4$). Distributions are shown at depths corresponding to a mean energy of the $^{11}C$ ion beam of 200 MeV/u in all the considered decelerators. A liquid hydrogen section of about 30 cm seems to give a good compromise between source size and yield.

In FIG. 12, the radial distributions of the $^{11}$C fragments for the different combinations of liquid hydrogen and polyethylene are presented at depths in the decelerator corresponding to the mean energy of the $^{11}$C ion beam of about 200 MeV/u. As seen in the figure, the peak heights of the distributions decrease as the liquid hydrogen section length increases and the radial distributions are correspondingly more spread out.

Figure 13:
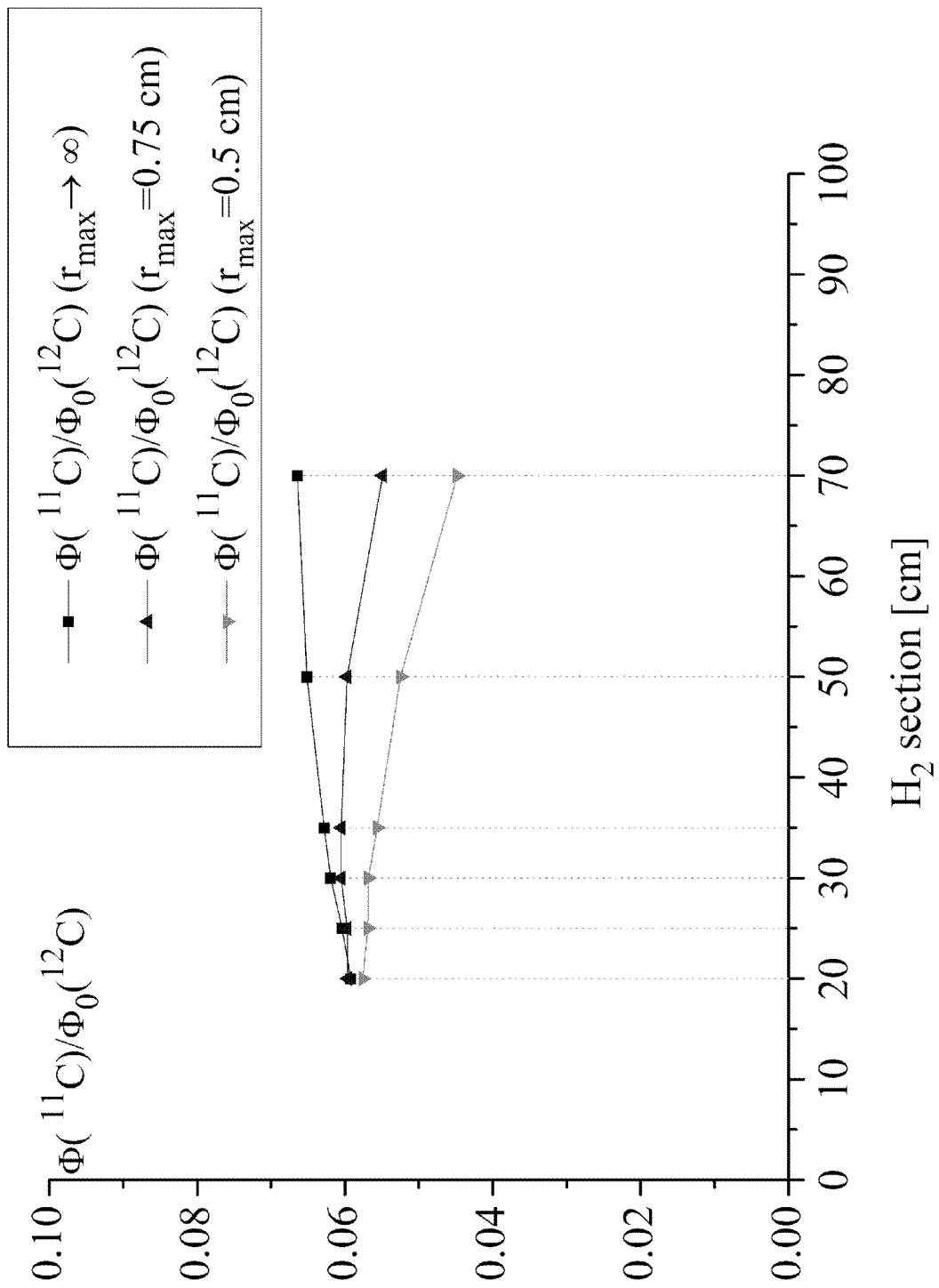
FIG. 13 illustrates fluence of $^{11}C$ fragments normalized to the incoming $^{12}C$ primary ion fluence calculated for different values of maximum radius (0.5, 0.75 cm and all radii). Solid straight lines are drawn between data points.

However, in order to determine the percentage of decrease in the $^{11}$C ion production as a function of a limited radial range (0.5 cm or 0.75 cm of maximum radius), a further analysis is conducted whose results are shown in FIG. 13. Solid squares illustrate the total production of $^{11}$C fragments when no restriction in the radial range is applied. Top triangles and reversed triangles show the fluence of $^{11}$C ions normalized to the incoming fluence of primary $^{12}$C particles for a radius limited to 0.75 and 0.5 cm respectively. In the former case, the production of $^{11}$C fragments seems to reach a peak value of about 6.3% with a liquid hydrogen section of approximately 35 cm, while in the latter case the production is initially rather constant and then starts to notably decrease from the peak value in correspondence of 20 cm of the liquid hydrogen.

From the results presented herein, it can be inferred that the optimal target material for the production of therapeutically useful $^{11}$C ion beams by projectile fragmentation of a primary $^{12}$C ion beam is a dual decelerator made of a combination of a first liquid hydrogen portion followed by a polyethylene section.

The first section has mainly the aim to enhance the $^{11}$C ion beam production and the following section is mainly used to decelerate the produced beam to the energy values needed in order to reach the desired tumour depth, while avoiding too much attenuation of the produced positron emitters. This last section might be made of binary plane parallel polyethylene slabs whose thickness combinations could be arranged to achieve the desired $^{11}$C ion beam mean energy with high accuracy.

Despite the smaller radial spread shown, the other elements and compounds investigated in this study have to be discarded because of their generally low production efficiency.

Due to the similar energy spread in all the considered materials, the selected length of the first liquid hydrogen section in the dual decelerator is then a compromise between the radial spread and the production efficiency of the $^{11}$C ion beam. Therefore, the selection of the optimal length of this section is also linked to the acceptance limits imposed by the beam line optics. As a result of the shown calculations, in case of a radial spread confined to ±0.5 cm, the optimal length of the liquid hydrogen section is 20 cm with a $^{11}$C ion production efficiency of about 5.5%; while if a higher tolerance of ±0.75 cm in the beam radial spread is allowed the production efficiency can be raised to values of about 6% with 35 cm of liquid hydrogen.

Despite the considerable width of the energy distributions of the $^{11}$C fragments shown for all the studied materials, the energy spread of the $^{11}$C ion beam is not considered as matter of concern in the present study. In fact, the energy spread of the $^{11}$C fragments (about 50 MeV/u) can be handled and reduced by inserting in the beam line a wedge filter with triangular shape that can reduce the energy spread of the produced $^{11}$C fragments to negligible values. In fact the produced $^{11}$C ions might be bent by the magnets in the beam line with a different radius according to the particle energies. The wedge filter can be then positioned in the beam line so as to let the fragments of a certain energy to correspondingly penetrate the appropriate wedge thickness that allow the reduction of the energy to a given value.

An aspect of the embodiments relates to a device or a system for producing an $^{11}$C radiation beam from a primary $^{12}$C beam, where the produced $^{11}$C radiation beam is useful in external beam radiation therapy. The device of the embodiments comprises a decelerator that comprises hydrogen in the form of $H_2$. When the incident primary $^{12}$C beam passes through the decelerator a $^{11}$C beam is produced by the device as disclosed herein.

The decelerator advantageously comprises liquid $H_2$ but could alternatively comprise the hydrogen in solid form or in a high pressurized gas form. In the latter case, the density of the pressurized hydrogen gas is preferably as high as possible and preferably close to the density of liquid hydrogen.

The decelerator of the device preferably comprises a so-called hydrogen section which then comprises the hydrogen, such as in liquid form. This hydrogen section could then be connected to a cooling device that keeps the hydrogen in liquid form. In such a case, it could be possible that only this hydrogen section of the decelerator needs to be temperature controlled.

As disclosed herein, the hydrogen section preferably has a thickness through which the beam travels through the hydrogen section that is in an interval of from 20 cm to 70 cm. The thickness is more preferably from 20 cm up to 40 cm and in particular from 20 cm up to 35 cm.

A particular embodiment uses a decelerator in the form of a multi-medium decelerator comprising the above mentioned hydrogen section followed by a decelerating section comprising a hydrogen rich material. The multi-medium decelerator then preferably first comprises the hydrogen section to achieve a fast initial $^{11}$C fluence build-up. The decelerating section is preferably provided downstream along the beam path of the hydrogen section. The decelerating section is then configured to modulate the mean energy of the beam to reach a desired target volume in a subject to be irradiated, preferably a mammalian subject and more preferably a human subject.

In an embodiment, the decelerating section comprises a hydrogen rich plastic material such as polyethylene as preferred example of such a solid hydrogen rich plastic material. Other examples of such solid hydrogen rich plastic materials include polypropylene. Generally, polyethylene is also referred to as polyethene in the art and is defined by the general structural formula:

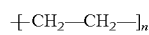

Correspondingly, polypropylene is also referred to as polypropene in the art and is defined by the general structural formula:

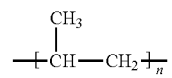

In an alternative embodiment, the decelerating section comprises a hydrogen rich liquid or fluid material, such as liquid methane, liquid propane or liquid ammonia. In such a case, the cooling device may, if necessary, also provide cooling effect to the decelerating section in order to keep the liquid material in liquid form at the operation temperature of the device.

The thickness of the decelerating section through which the beam travels is preferably selected, as mentioned herein, to module the range of the $^{11}$C beam to reach a target depth in a subject to be irradiated. This can be achieved by providing the decelerating section in the form of a binary system of multiple slices or slabs of the hydrogen rich material. Such a binary system is schematically illustrated in the lower half of FIGS. 17 and 18. In those figures, the decelerating section is exemplified by a binary system of 8 slices. The depth of the produced $^{11}$C beam in the subject to be irradiated is then dependent on the number of such slices the beam passes through the decelerating section as indicated in these figures. Thus, in such a case a maximum range shift of about $$\sum_{i=0}^{7} 2^i = 255 \text{ mm}$$

is possible. Generally, the decelerating section can reduce the range of the $^{11}$C beam in the subject body with about $$\sum_{i=0}^{N-1} 2^i \text{ mm,}$$

wherein N denotes the number of slices of the hydrogen rich material.

In a particular embodiment, the device also comprises or is connected to a slice adjuster that is configured to adjust the number of slices of the hydrogen rich material that are present in a beam path through the binary system to thereby achieve a modulation of the range of the $^{11}$C beam. The slice adjuster then preferably performs such an adjustment based on a control signal received from a user input or from a previously programmed irradiation scheme to be used for the current subject.

An advantage of the present embodiments is that the device is capable of producing a $^{11}$C beam of sufficient quality to be used not only for external radiation therapy but also for simultaneous dose delivery verification using, for instance, positron emission tomography (PET) or positron emission tomography-computer tomography (PET-CT) imaging.

Figure 15:
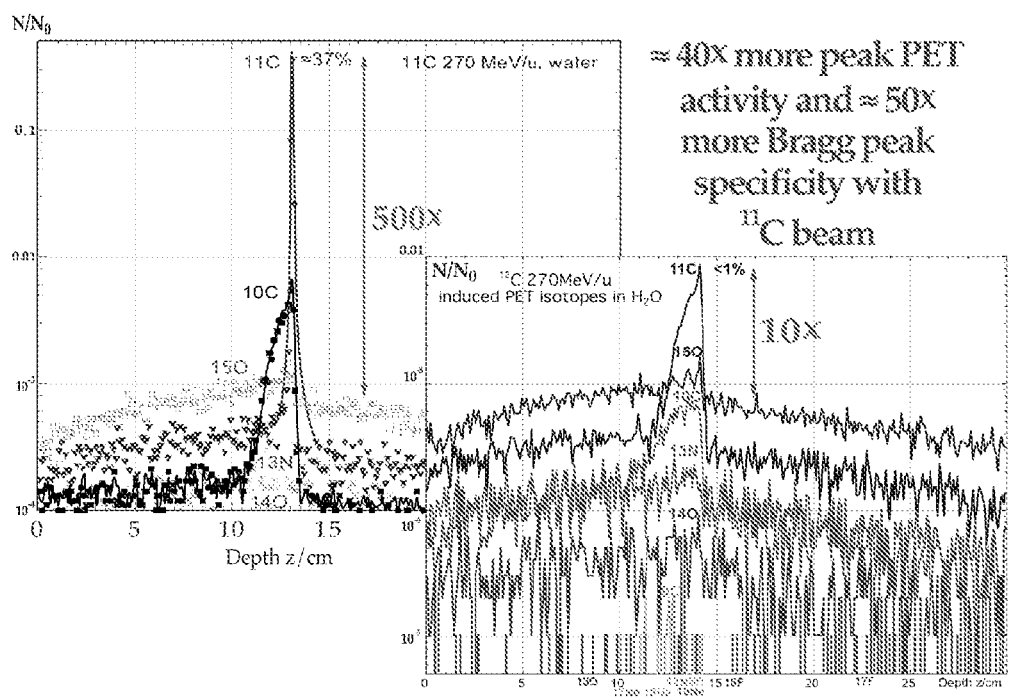
FIG. 15 is a comparison of the PET activity induced by $^{12}$C and $^{11}$C ion beams in water. A considerably higher sensitivity to detect the primary carbon ion Bragg peak with the $^{11}$C beam is clearly seen. This is of considerable importance for accurate in vivo dose delivery imaging far beyond what can be done with $^{12}$C. Many of the low level components of activity outside the Bragg peak have a fast decay and may be lost when imaging outside the treatment area.

FIG. 15 illustrates a comparison of the PET activity induced by $^{12}$C and $^{11}$C beams in water. The figure clearly shows that a considerably higher sensitivity to detect the primary carbon ion Bragg peak is achieved with the $^{11}$C beam. Hence, the $^{11}$C beam enable accurate in vivo dose delivery imaging far beyond what is possible with the $^{12}$C beam.

Figure 14:
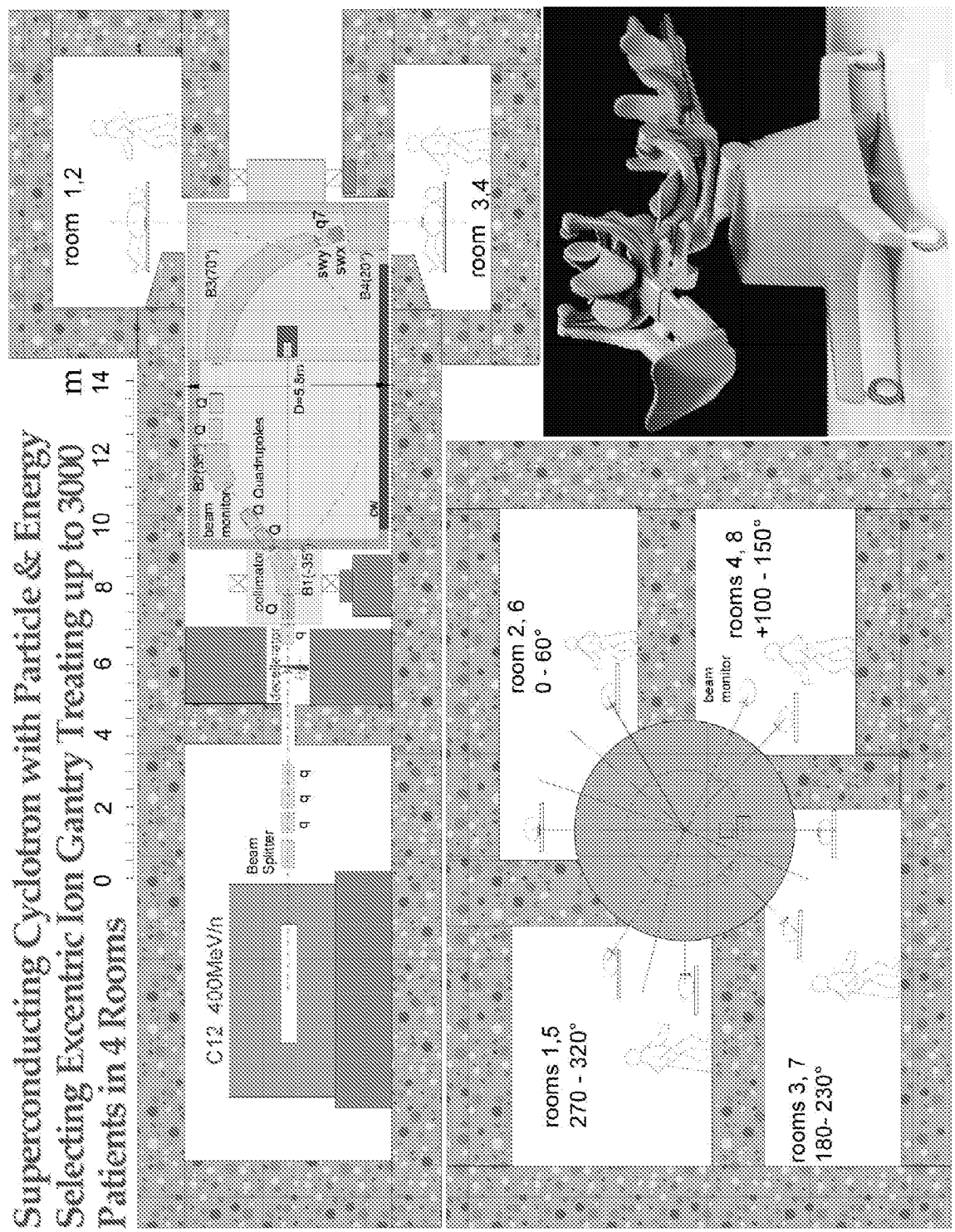
FIG. 14 is a cross section through the Superconducting Cyclotron with the Particle & Energy Selecting Excentric Ion Gantry capable of treating patients in 4 surrounding rooms as shown in the lower left panel. The four treatment rooms with protons to carbon ions allow a 10-12 min set up time, and a 2-3 min treatment time/room. In this way a total 12-16 patients/hour, 100-120 patients/day and 2 500 patients/year (at 10-12 fractions/patient) can conveniently be treated. In the figure the decelerating graphite range shifter is indicated where $^{11}$C can be produced in therapeutic quantities allowing 50 fold accuracy in Bragg peak imaging. The lower right panel shows a close up of the stereotactic treatment couch that can be used to dock the patient both to the PET-CT camera and the therapy unit. A compact decelerator is shown in the beam line just before the gantry. The somewhat degraded beam from the decelerator is collected by spectrographic magnets that pick up the central high fluence part of the $^{11}$C ions and after the first bend also the beam components with low and high energy deviations may be analyzed so the preferably peak of forward directed ions are only allowed to continue through the bending magnet to the patient.
Figure 16:
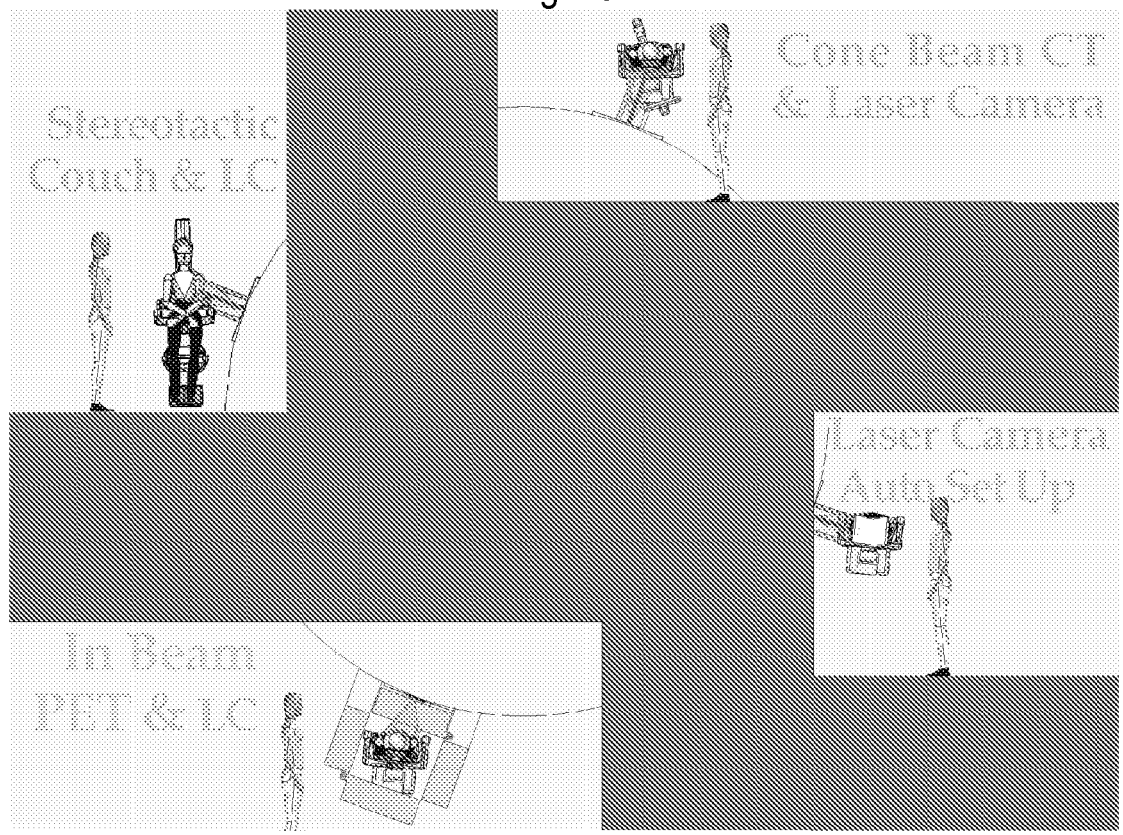
FIG. 16 is a cross sectional view through the excentric gantry ($\approx$6 m diameter) with the four treatment rooms surrounding it. Each room has about ±60 degree flexibility in selection of beam direction since the patient couch can be rotated more than 180°. In the lower right room the treatment will start in a few minutes, in the upper left room the patient is about to leave the treatment room and in the lower left room the patient is being studied by PET imaging during and after treatment whereas in the upper right room the treatment set up is about to be finished. In this way about 16 patients per hour can be treated with one excentric gantry.

The beam radiation therapy based on the produced $^{11}$C radiation beam can advantageously be used in connection with an excentric gantry system as disclosed in WO 2005/053794 and further illustrated in FIGS. 14 and 16.

Figure 17:
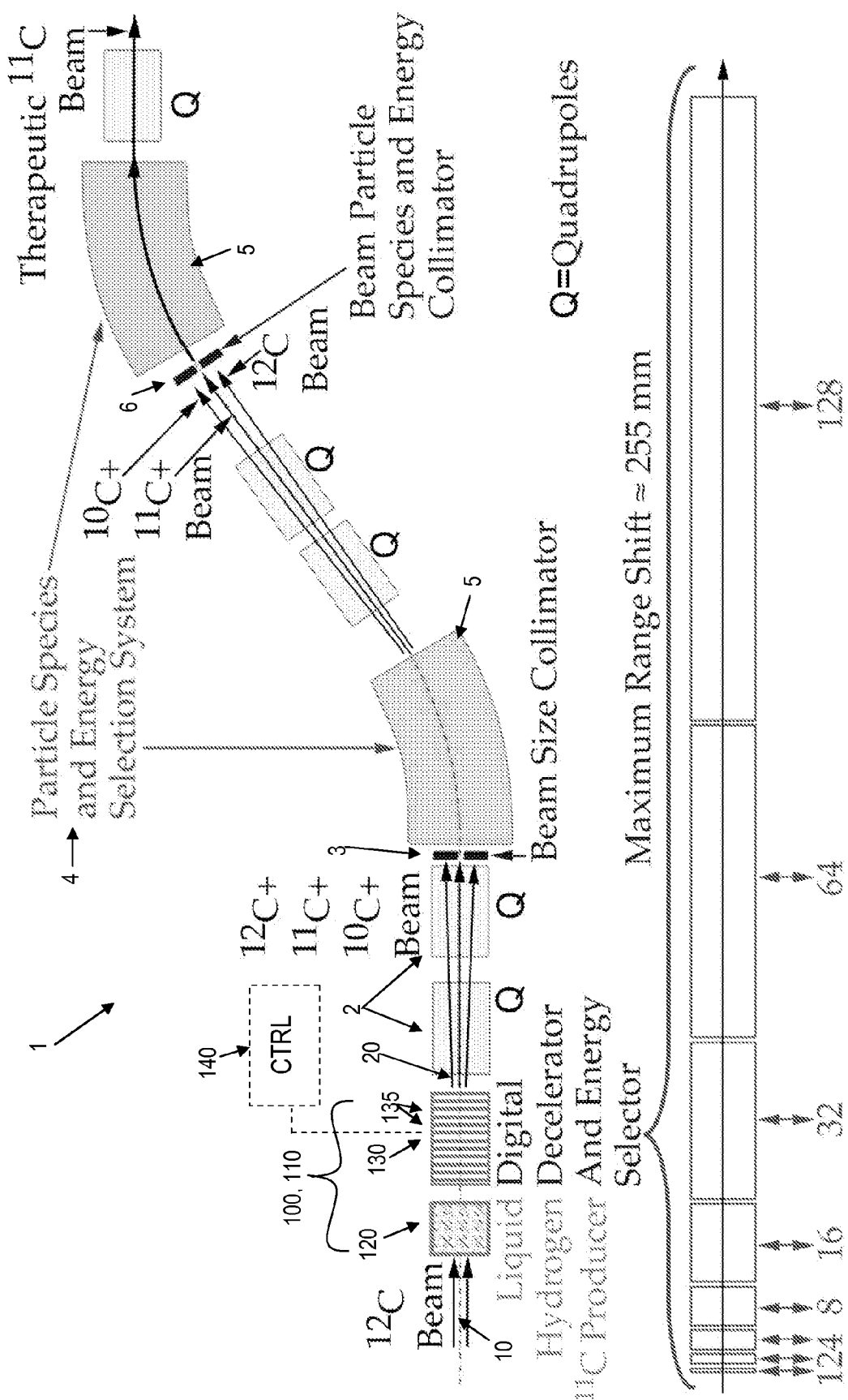
FIG. 17 is a schematic drawing illustrating radiation system equipped with a device for producing an ion beam according to an embodiment arranged in connection with a beam guiding system.
Figure 18:
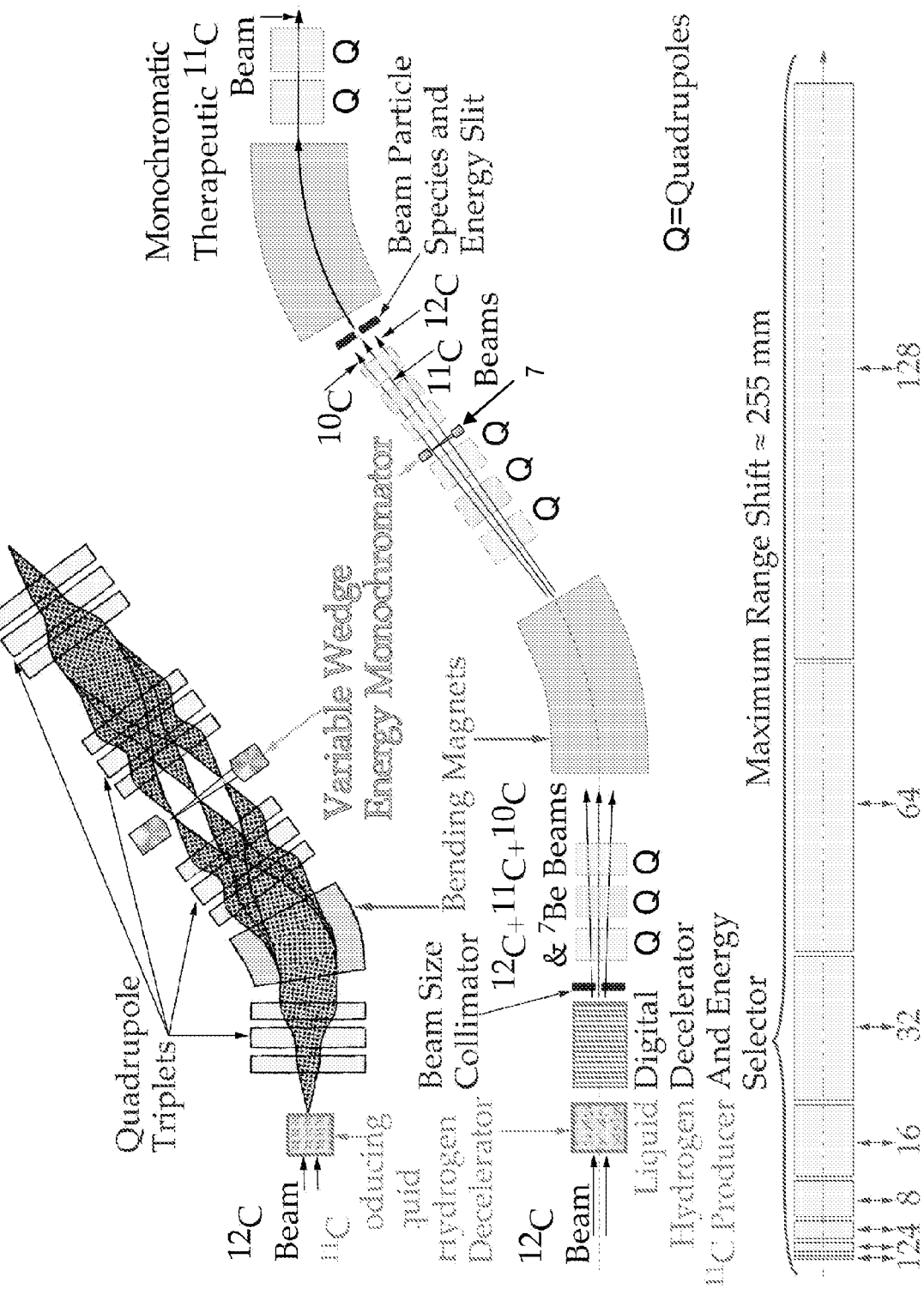
FIG. 18 is a schematic drawing illustrating radiation system equipped with a device for producing an ion beam according to an embodiment arranged in connection with a beam guiding system, describing the beam optics of a variable wedge filter monocromator.
Figure 19:
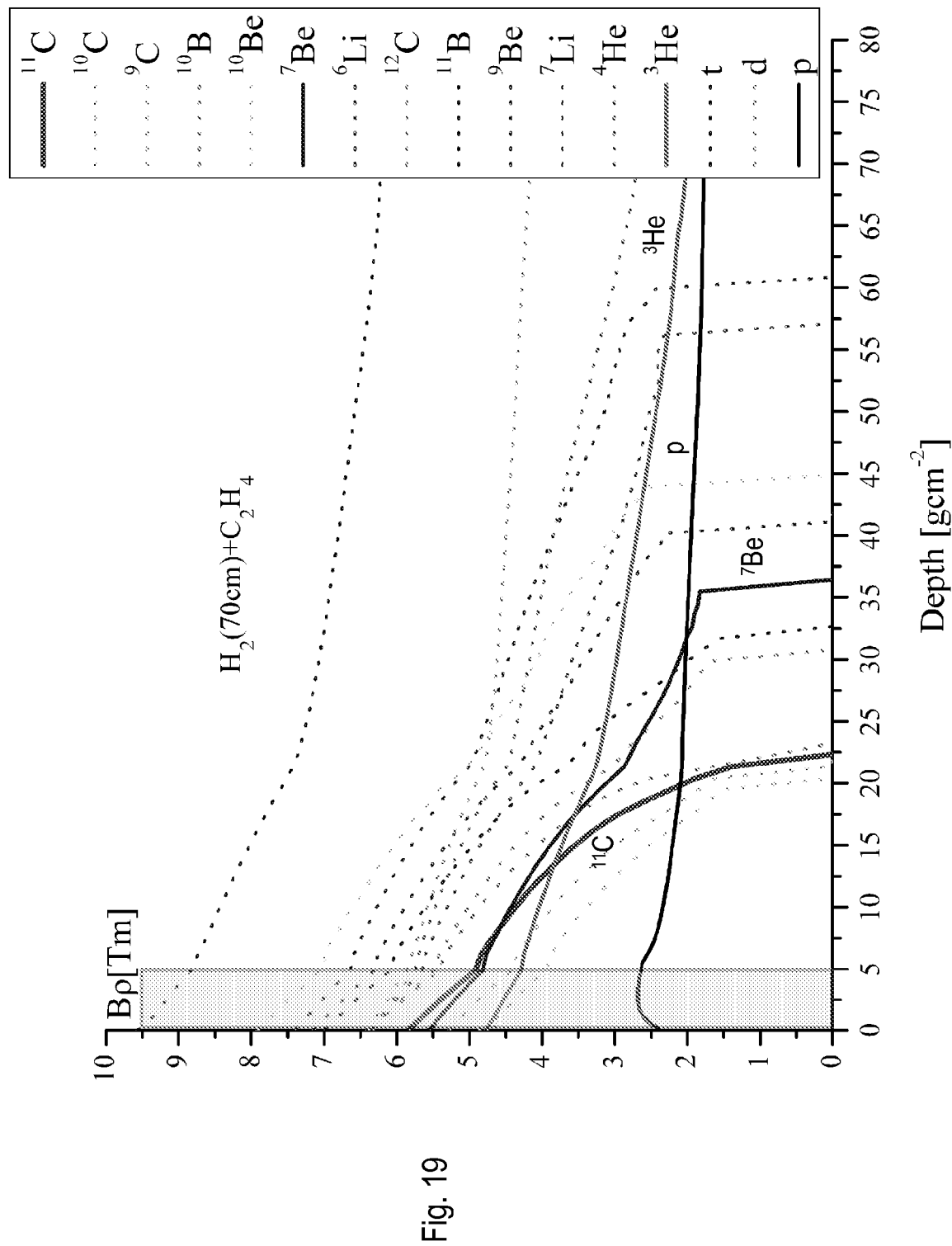
FIG. 19 illustrates magnetic rigidity of the particles produced by the fragmentation of a $^{12}$C ion beam in a decelerator as a function of the depth in the target. The considered decelerator is composed by a first liquid hydrogen section (70 cm) followed by a polyethylene ($C_2H_4$) section. Crossing points of the $^{11}$C magnetic rigidity curve with the magnetic rigidity curves of $^{7}$Be and $^{3}$He fragments are clearly seen at about 8 gcm$^{-2}$ and 13 gcm$^{-2}$ of depth respectively.
Figure 20A:
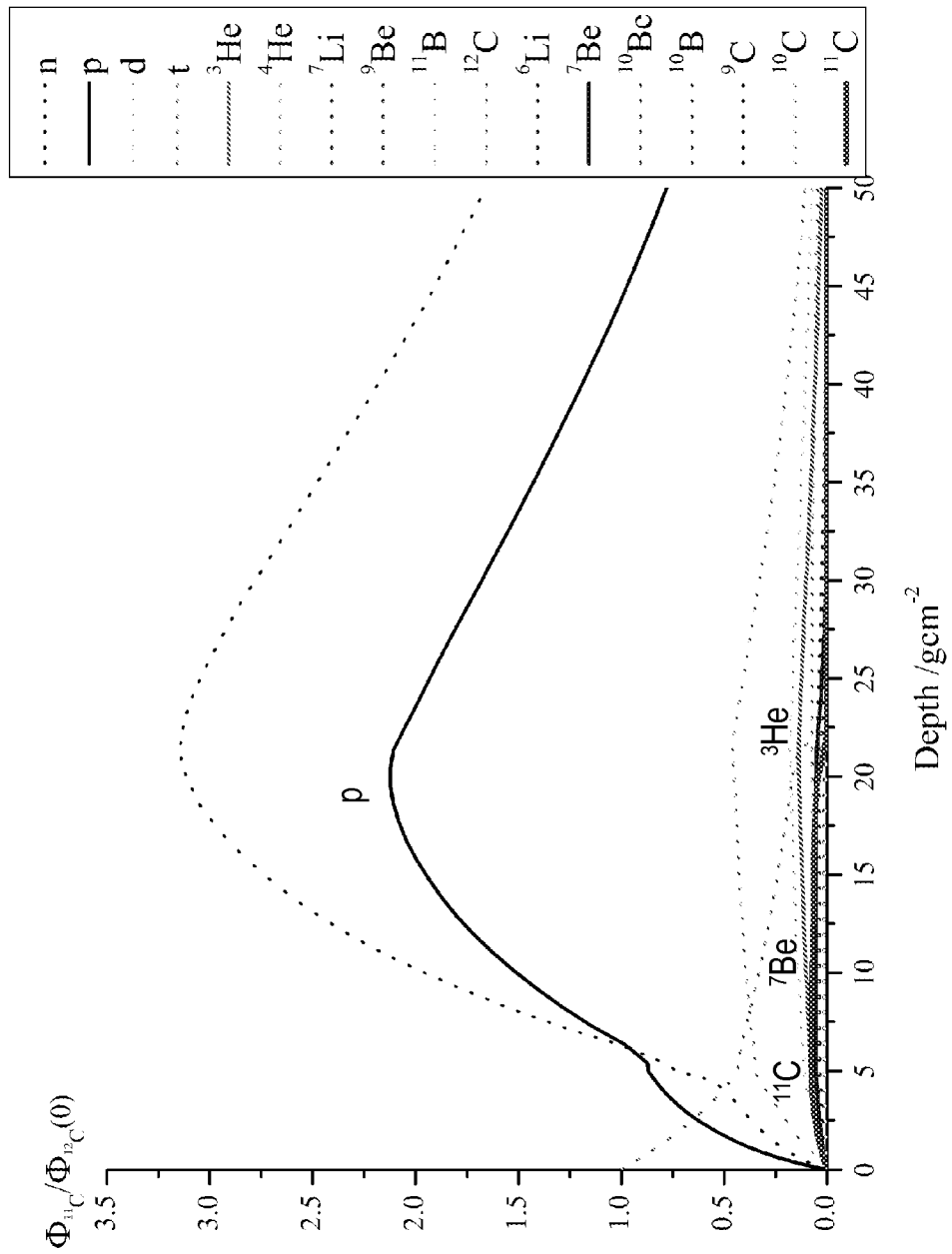
FIGS. 20A and 20B illustrate normalized fluence of the fragments produced in the decelerator as a function of the depth in the target (FIG. 20A). The decelerator is composed by 70 cm of liquid hydrogen followed by polyethylene. The relative proportion of $^{7}$Be and $^{3}$He fragments with respect to $^{11}$C ions is better visualized in the close-up shown in FIG. 20B.
Figure 20B:
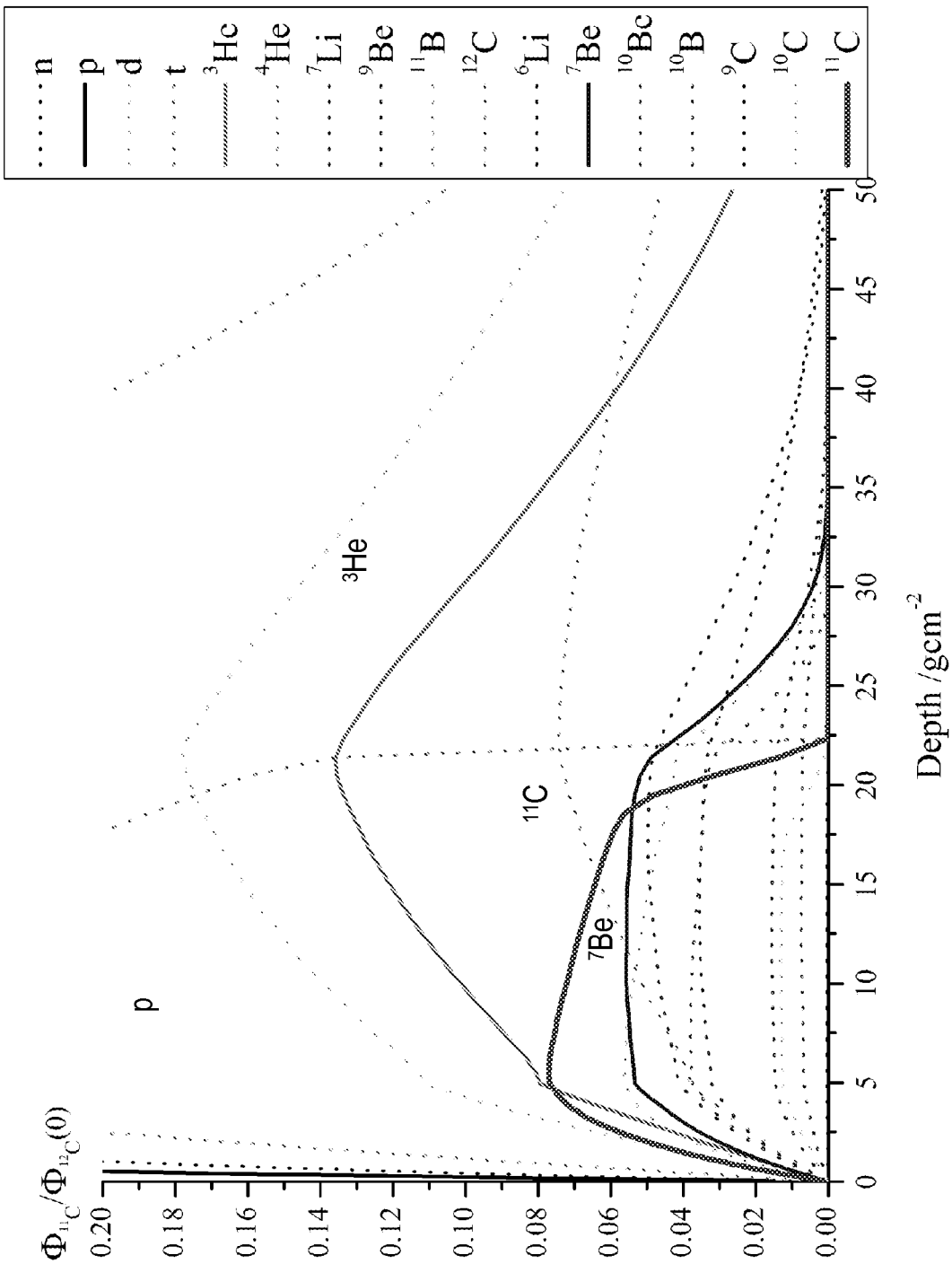

FIGS. 17 and 18 are schematic illustrations of embodiments of a radiation system 1 comprising a device 100 according to the invention for producing useful $^{11}$C radiation beam 20. The device 100 comprises a decelerator 110 with a hydrogen section 120, such as in the form of a liquid hydrogen based $^{11}$C producer as disclosed herein into which a $^{12}$C beam 10 incidents. The device 100 comprises a chamber containing the liquid hydrogen and optionally comprises vacuum windows in either ends, i.e. input end and output end of the device 100. Cooling fingers may protrude from the lower or upper parts of the chamber, i.e. outside of the path of the radiation beam. These cooling fingers keep the enclosed hydrogen in liquid form. The formed radiation beam is generally a mixed $^{10\text{-}11\text{-}12}$C beam that enters a following decelerating section 130, preferably in the form of a digital decelerator and energy selector. This decelerating section 130 can provide range shifting with, for instance, 8 decelerator slices 135 reducing the range $2^n$ mm, where n=0, 1, . . . , 7. The output radiation beam 20 from the decelerator 110 preferably enters a set of quadropoles 2 for focusing the radiation beam 20. The mixed $^{10\text{-}11\text{-}12}$C beam 20 then preferably enters a beam size collimator 3 providing angular limitation. A set of bending magnets 5 and a further collimator 6 are preferably arranged for achieving a particle species and energy selection system 4 to finally output a therapeutic $^{11}$C beam 20 quality useful for external beam radiation therapy.

The figure also indicates the previously discussed slice adjuster 140, represented by a controller (ctrl), that can be used to adjust the number of slices present in the binary system of the decelerating section 130.

Figure 22:
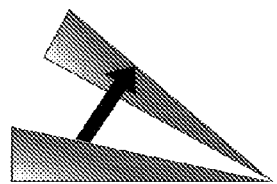
FIG. 22 illustrates possible designs of a flexible wedge system for variable $^{11}$C energies.
Figure 22:
Figure 22:
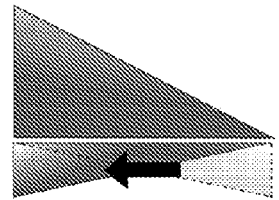
Figure 22:
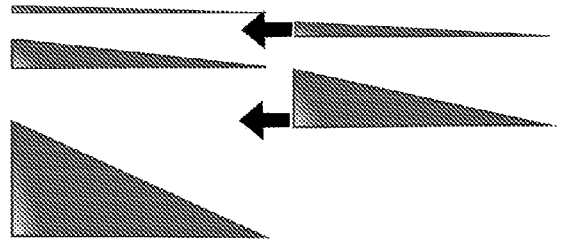

In a particular embodiment as illustrated in FIG. 18, the radiation system 1 can comprise a wedge filter or wedge-shaped decelerator 7 as disclosed herein and further illustrated in FIGS. 21 and 22. The wedge filter 7 preferably forms part of the particle species and energy selection system 4. This wedge filter 7 can then be arranged downstream of the first bending magnet but upstream of the beam particle species and energy collimator 6.

In order to minimize the energy spread of the produced $^{11}$C beam it is possible to insert the wedge-shaped decelerator in the dispersion plane of the bending magnet that is also used to separate the different ion species (FIGS. 17 and 18). By turning the thick wedge side away from the center of curvature of the particle orbits in the bending magnets it is possible to reduce the energy of the high energy portion of the ion spectrum so it coincides with the low energy portion and in between the energy on the exit side is always brought to this low energy portion of the $^{11}$C ion spectrum, as shown in FIG. 21. At the downstream end of the wedge filter the $^{11}$C energy spread can thus be reduced to a fraction of 1% so the range can be accurately defined in the patient. However, for production of variable $^{11}$C ion beam energies the wedge angle is preferably variable. In a first approximation this could be achieved by tilting or rotating the wedge so the particle path gets longer, see FIG. 22:1. However, this does not give much flexibility. Instead three more flexible variable wedge filter solutions are proposed. FIG. 22:2 is a liquid or soft clay like material wedge with solid walls, FIG. 22:3 is a combination of two axially rotatable wedges which can span a wide range of variable effective wedges angles, and FIG. 22:4 finally is a digitally variable wedge similar to the decelerator design in FIG. 18. Both the methods in FIGS. 22:2 and 22:3 are continuously variable and can be designed to be non linear if needed. The digitally variable wedge can also contain non linear wedges and can have arbitrary fine correction possibilities depending on the desired exit energy given by the setting of the digital decelerator in FIGS. 17 and 18. A system like in FIG. 18 with a variable wedge according to FIG. 22 can therefore make arbitrary monoenergetic $^{11}$C ion beams covering the whole range of clinically desirable penetration depths from about 30 down to a few cm in tissue.

To minimize the angular spread in the wedge it is preferred to have a low atomic number wedge material like liquid hydrogen or polyethylene or even lithium or beryllium. The advantage of a liquid hydrogen wedge could be minimal multiple scatter and a higher $^{11}$C beam fluence compared to other wedge materials, since it already achieved better results in the production of the beam. This would mean that the beam intensity of the $^{11}$C beam at the exit of the wedge could be further optimized.

Interestingly, the wedge thickness is maximum at intermediate energies since the stopping power increases rapidly at low energies and less thick wedges are needed similar as at high energies where the energy spread instead is small and less thick wedges are needed for that reason.

As is illustrated in FIGS. 17 and 18, the radiation system 1 may include further quadropoles, such as present in the particle species and energy selection system 4 and/or downstream of the particle species and energy selection system 4. Although not shown in FIGS. 17 and 18 but indicated in FIG. 14, the radiation system preferably also comprises or is connected to a $^{12}$C beam provider configured to be implemented as an ion source configured to produce $^{12}$C ions and a cyclotron configured to accelerate the $^{12}$C ions to form the primary $^{12}$C beam. The ion acceleration is preferably designed to produce the primary $^{12}$C beam having a target energy, which is advantageously selected to be in a range of at least 360 MeV/u, and preferably as high as 430 MeV/u to produce a high fluence of $^{11}C$ also at high energies, in particular the embodiment should preferably be in the range of 400 to 430 MeV/u.

The embodiments also define a method of producing a $^{11}C$ beam from a primary $^{12}C$ beam. The method comprises directing the primary $^{12}C$ beam onto a decelerator comprising hydrogen ($H_2$) to form the $^{11}C$ beam that is suitable for external radiation therapy. The decelerator is preferably designed as defined in the foregoing.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

The invention claimed is:

1. A device for producing a $^{11}C$ beam from a primary $^{12}C$ beam, said device comprises a decelerator comprising hydrogen, $H_2$, and configured to output said $^{11}C$ beam suitable for external radiation therapy from said primary $^{12}C$ beam incident on said decelerator, wherein said decelerator is a multi-medium decelerator comprising a hydrogen section followed by a decelerating section comprising a hydrogen rich material.

2. The device according to claim 1, wherein said decelerator comprises liquid $H_2$.

3. The device according to claim 1, wherein said decelerator comprises a hydrogen section comprising said hydrogen $H_2$ and having a thickness in an interval of from 20cm up to 70 cm.

4. The device according to claim 3, wherein said decelerator comprises said hydrogen section comprising said hydrogen $H_2$ and having said thickness in an interval of from 20 cm up to 35 cm.

5. The device according to claim 1, wherein said decelerating section comprises a hydrogen rich plastic material.

6. The device according to claim 5, wherein said decelerating section comprises a hydrogen rich plastic material selected from the group of polyethylene and polypropylene.

7. The device according to claim 1, wherein said decelerating section comprises a hydrogen rich material selected from the group of liquid methane, liquid propane and liquid ammonia.

8. The device according to claim 1, wherein said decelerating section has a thickness selected to modulate a range of said $^{11}C$ beam to reach a target depth in a subject to be irradiated by said $^{11}C$ beam.

9. The device according to claim 1, wherein said decelerating section is in the form of a binary system of multiple slices of said hydrogen rich material.

10. The device according to claim 9, further comprising a slice adjuster configured to adjust a number of slices of said hydrogen rich material that are present in a beam path through said binary system to achieve a modulation of a range of said $^{11}C$ beam.

11. The device according to claim 10, wherein said slice adjuster is configured to adjust said number N of slices of said hydrogen rich material to reduce said range of said $^{11}C$ beam with an amount of $$\sum_{i=0}^{N-1} 2^i \text{ mm.}$$

12. The device according to claim 1, wherein said decelerator is configured to output said $^{11}C$ beam suitable for simultaneous external radiation therapy and dose delivery verification using positron emission tomography or positron emission tomography-computed tomography imaging.

13. A radiation system comprising:
a device according to claim 1 to produce a $^{11}C$ beam from a primary $^{12}C$ beam;
a set of quadropoles downstream of said device and configured to focus said $^{11}C$ beam;
a beam size collimator downstream of said set of quadropoles and configured to impose an angular limitation to said $^{11}C$ beam; and
a particle species and energy selection system downstream of said beam size collimator and configured to output a therapeutic $^{11}C$ beam having a beam quality useful for external radiation therapy.

14. The radiation system according to claim 13, wherein said particle species and energy selection system comprises a set of bending magnets and a beam particle species and energy collimator.

15. The radiation system according to claim 14, wherein said particle species and energy selection system further comprises a variable wedge filter configured to reduce an energy spread of said $^{11}C$ beam.

16. The radiation system according to claim 15, wherein said variable wedge filter is in the form of a variable liquid medium wedge filter with solid walls.

17. The radiation system according to claim 16, wherein said variable wedge filter is in the form of a variable liquid hydrogen, $H_2$, wedge filter.

18. The radiation system according to claim 15, wherein said variable wedge filter comprises two axially rotatable wedges.

19. The radiation system according to claim 15, wherein said variable wedge filter is a multi-layer wedge.

20. The radiation system according to claim 13, further comprising a $^{12}C$ beam provider configured to provide said primary $^{12}C$ beam.

21. The radiation system according to claim 20, wherein said $^{12}C$ beam provider comprises an ion source configured to produce $^{12}C$ ions and a cyclotron configured to accelerate said $^{12}C$ ions to form said primary $^{12}C$ beam.

22. A method of producing a $^{11}C$ beam from a primary $^{12}C$ beam, said method comprising directing said primary $^{12}C$ beam onto a device as defined in claim 1, said $^{11}C$ beam suitable for external radiation therapy exiting said decelerator.

23. A radiation system comprising:
a device for producing a $^{11}C$ beam from a primary $^{12}C$ beam, said device comprises a decelerator comprising hydrogen, $H_2$, and configured to output said $^{11}C$ beam suitable for external radiation therapy from said primary $^{12}C$ beam incident on said decelerator;
a set of quadropoles downstream of said device and configured to focus said $^{11}C$ beam;
a beam size collimator downstream of said set of quadropoles and configured to impose an angular limitation to said $^{11}C$ beam; and
a particle species and energy selection system downstream of said beam size collimator and configured to output a therapeutic $^{11}$C beam having a beam quality useful for external radiation therapy, wherein said particle species and energy selection system comprises:
a set of bending magnets,
a beam particle species,
an energy collimator, and
a variable wedge filter in the form of a variable liquid hydrogen, $H_2$, wedge filter with solid walls and configured to reduce an energy spread of said $^{11}$C beam.

* * * * *